US 6,548,023 B1

(12) United States Patent
Matsuo et al.

(10) Patent No.: US 6,548,023 B1
(45) Date of Patent: Apr. 15, 2003

(54) GAS SENSOR

(75) Inventors: Kouji Matsuo, Aichi (JP); Shoji Akatsuka, Aichi (JP); Shoichi Ohtsuki, Aichi (JP); Satoshi Ishikawa, Aichi (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/334,722

(22) Filed: Jun. 17, 1999

(30) Foreign Application Priority Data

Jun. 18, 1998 (JP) .......................... 10-171438

(51) Int. Cl.$^7$ .................. G01N 7/00; G01N 27/00; G01N 31/12
(52) U.S. Cl. ............... 422/83; 422/94; 422/98
(58) Field of Search .................. 422/83, 94, 98; 204/415; 338/34; 73/23, 23.2

(56) References Cited

U.S. PATENT DOCUMENTS

| 3,962,153 A | | 6/1976 | Gore .................. 260/2.5 R |
|---|---|---|---|
| 4,578,174 A | * | 3/1986 | Kato et al. ............... 204/429 |
| 4,596,837 A | | 6/1986 | Yamamoto et al. ......... 521/145 |
| 4,756,885 A | * | 7/1988 | Raff et al. .................. 422/98 |
| 4,818,364 A | * | 4/1989 | Weber et al. ............... 204/427 |
| 4,870,855 A | * | 10/1989 | Shafer ......................... 73/23 |
| 5,304,976 A | * | 4/1994 | Ono ............................ 338/34 |
| 5,462,586 A | | 10/1995 | Sugiyama et al. ............ 96/13 |
| 5,573,650 A | * | 11/1996 | Fukaya et al. ............. 204/424 |
| 5,762,771 A | * | 6/1998 | Yamada et al. ............ 204/428 |
| 5,795,454 A | * | 8/1998 | Friese et al. ............... 204/424 |
| 5,830,339 A | * | 11/1998 | Watanabe et al. ......... 204/426 |
| 5,874,664 A | | 2/1999 | Watanabe et al. |
| 5,900,129 A | * | 5/1999 | Tsuji et al. ............... 204/427 |
| 5,948,963 A | * | 9/1999 | Kato et al. ................. 73/23.2 |
| 5,985,118 A | * | 11/1999 | Makino et al. ............ 204/426 |
| 6,083,371 A | * | 7/2000 | Weyl et al. ............... 204/426 |
| 6,165,336 A | * | 12/2000 | Maki et al. ............... 204/415 |
| 6,178,806 B1 | * | 1/2001 | Watanabe et al. .......... 73/23.32 |
| 6,214,186 B1 | * | 4/2001 | Watanabe et al. .......... 204/428 |
| 6,222,372 B1 | * | 4/2001 | Fukaya et al. ............. 324/464 |

FOREIGN PATENT DOCUMENTS

| DE | 196 05 290 | 8/1997 |
|---|---|---|
| EP | 0 661 336 A1 | 7/1995 |
| GB | 1355373 | 6/1974 |
| JP | 42-13560 | 8/1942 |
| JP | 51-18991 | 6/1976 |
| JP | 56-17216 | 4/1981 |
| JP | 56-45773 | 10/1981 |
| JP | 58-145735 | 8/1983 |
| JP | 59-152825 | 8/1984 |
| JP | 3-221541 | 9/1991 |
| JP | 4-164245 | 6/1992 |
| JP | 5-34301 | 2/1993 |
| JP | 5-196598 | 8/1993 |
| JP | 7-126428 | 5/1995 |
| JP | 7-196831 | 8/1995 |
| JP | 8-201328 | 8/1996 |
| JP | 9-210953 | 8/1997 |

\* cited by examiner

Primary Examiner—Jan Ludlow
Assistant Examiner—Brian Sines
(74) Attorney, Agent, or Firm—Morgan, Lewis & Bockius LLP

(57) ABSTRACT

In a gas sensor, a casing which accommodates a sensing element includes an inner cylindrical member and an outer cylindrical member which are caulked together by means of a caulked portion. The Vickers hardness H1 of the inner cylindrical member is Hv 250 to 430; the Vickers hardness H2 of the outer cylindrical member is Hv 160 to 330; and the hardness difference "H1–H2" is not less than 30. Through employment of the above ranges of H1 and H2, the caulked portion can maintain good airtightness even in a working environment involving, for example, thermal shocks.

8 Claims, 19 Drawing Sheets

Fig. 12
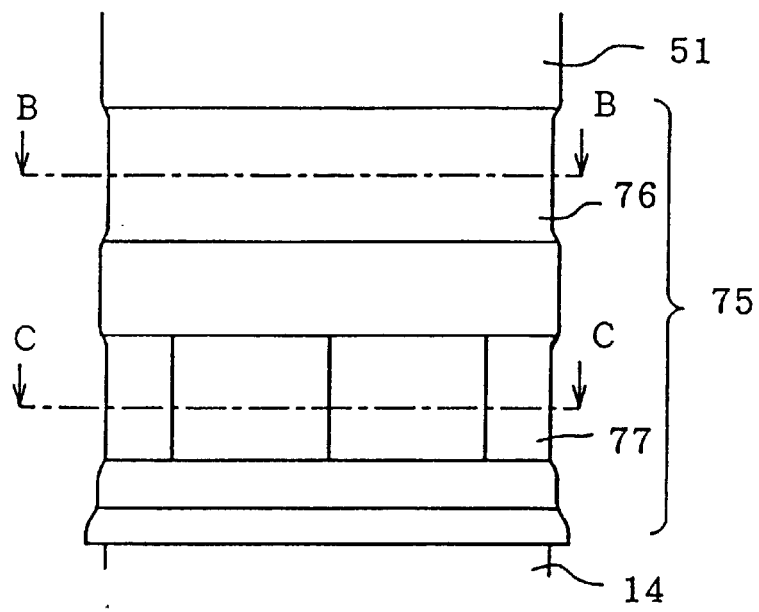
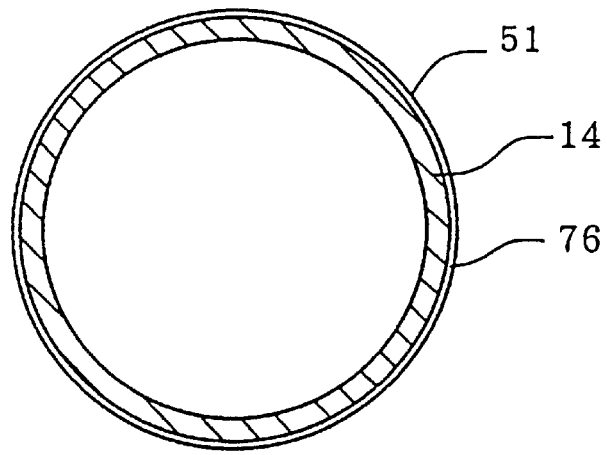
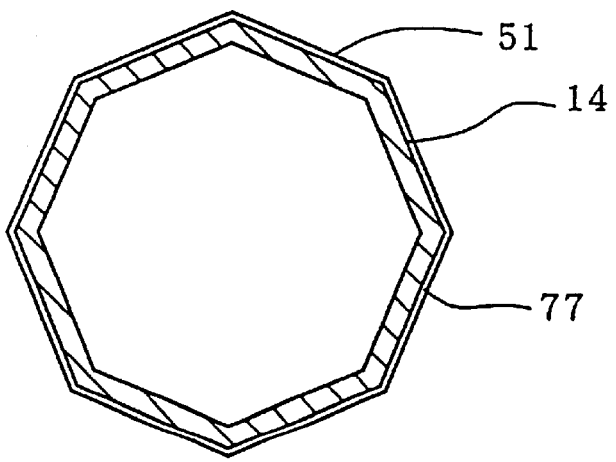

US 6,548,023 B1

GAS SENSOR

This application claims the benefit of Japanese Patent Application No. Hei. 10-171438, filed in Japan on Jun. 18, 1998, which is hereby incorporated by reference.

BACKGROUND OF THE INVENTION

1. Field of the Invention

The present invention relates to a gas sensor, such as an oxygen sensor, HC sensor, or NOx sensor, for detecting a component in gas to be measured, 2. Description of the Related Art Conventional gas sensors have a structure in which a metallic casing accommodates a bar-like or cylindrical sensing element which has a sensing portion formed at its tip end and is adapted to detect a component in gas. The metallic casing includes a combination of a plurality of cylindrical members, such as a metallic shell, a protector, an inner cylindrical member, and an outer cylindrical member. The metallic shell has a screw portion formed on its outer surface that is used for attachment. The protector is connected to the metallic shell in such a manner as to cover the sensing portion of a sensing element which projects from one end of the metallic shell. The inner cylindrical member is connected to the other end of the metallic shell and adapted to cover the sensing element which extends rearward from the metallic shell; i.e., opposite the protector with respect to the metallic shell. The outer cylindrical member is connected to a rear end portion of the inner cylindrical member and allows a lead wire from the sensing element to extend rearward from a rear open end thereof.

The inner cylindrical member and the outer cylindrical member are made of, for example, stainless steel, In many gas sensors, the inner and outer cylindrical members are caulked together. Specifically, an end portion of the outer cylindrical member is fitted onto a corresponding end portion of the inner cylindrical member to thereby form an overlap zone. In the overlap zone, the outer cylindrical member is circumferentially caulked to the inner cylindrical member, thereby forming an annular caulked portion and thus bonding the members in an airtight manner.

Adjusting the hardness of the inner and outer cylindrical members before the inner and outer cylindrical members are caulked as described above is an important measure for attaining a caulked seal which is free from play or loosening and exhibits excellent airtightness. For example, Japanese Patent Application Laid-Open (kokai) No. 9-210953 describes adjustment of the hardness of a stainless steel inner cylindrical member (inner cover) of an oxygen sensor to Hv 150 to 350 on the Vickers scale and the hardness of a stainless steel outer cylindrical member (outer cover) of the oxygen sensor to Hv 100 to 300 on the Vickers scale in order to attain a tightly caulked seal having excellent resistance to vibration. The publication also describes an embodiment in which the outer cylindrical member having a thickness of 0.5 mm a hardness of Hv 150 and the inner cylindrical member having a thickness of 0.7 mm has a hardness of Hv 240.

Gas sensors, e.g., oxygen sensors are often mounted on an exhaust pipe or exhaust manifold through which high-temperature exhaust gas flows, Accordingly, sensor temperature becomes approximately equal to ambient temperature in an idle state, whereas it increases to hundreds of degrees centigrade in high-speed high-load operation. Therefore, the oxygen sensor is repeatedly subjected to a considerably severe thermal shock. The publication described above discusses the effects of the caulked seal being subjected to vibration or water splashes (or submergence), but fails to address in detail the effects of thermal shock. The inventors of the present invention carried out intensive studies, and as a result, found that when the outer and inner cylindrical members assume the values of hardness appearing in the publication, in some cases the caulked portion fails to maintain good airtightness after being subjected to a severe thermal history.

An object of the present invention is to provide a gas sensor having a structure such that an inner cylindrical member and an outer cylindrical member, which cover a sensing element, are caulked together to form a caulked portion, and the caulked portion can maintain good airtightness even in a working environment involving, for example, thermal shocks.

SUMMARY OF THE INVENTION

To achieve the above object, the present invention provides a gas sensor comprising a bar-like or cylindrical sensing element and a cylindrical casing. The sensing element has a sensing portion formed at a tip end portion thereof and is adapted to detect a component in gas to be measured (gas under measurement).

The cylindrical casing covers the sensing element while the gas under measurement is permitted to flow therethrough to the sensing portion. The casing includes at least two axially adjacent cylindrical members. An end portion of one cylindrical member (hereinafter referred to as an inner member) is disposed within a corresponding end portion of the other cylindrical member (hereinafter referred to as an outer member) to thereby form an overlap zone.

The inner cylindrical member has a Vickers hardness H1 of Hv 250 to 430; the outer cylindrical member has a Vickers hardness H2 of Hv 160 to 330; and the hardness difference "H1–H2" therebetween is not less than 30. In the overlap zone, the inner cylindrical member and the outer cylindrical member are circumferentially caulked in an airtight manner.

According to the above-described structure of the gas sensor,the inner cylindrical member and the outer cylindrical member assume hardness values within the above ranges, so that the caulked portion can maintain good airtightness even in a working environment involving, for example, thermal shocks.

A key structural point of the present invention is that the Vickers hardness H2 of the outer cylindrical member assumes a value of at least Hv 160, which is higher than that disclosed in the aforementioned publication. Through increase in the Vickers hardness H2 of the outer cylindrical member, the hardness of the caulked portion is increased, thereby suppressing deformation of the caulked portion caused by thermal stress induced therein during exposure to heat cycles, and thus preventing the caulked portion from loosening, while yielding a resultant improvement in airtightness. Further, the Vickers hardness H1 of the inner cylindrical member is adjusted to not less than Hv 250, and the hardness difference "H1–H2" between the inner and outer cylindrical members is set to not less than 30. Thus, when the outer cylindrical member having the above high hardness is caulked onto the inner cylindrical member, the inner cylindrical member can sufficiently receive the caulking force, whereby the caulked portion can attain strong adhesion.

When the Vickers hardness H2 of the outer cylindrical member is less than Hv 160, the thermal shock resistance of the caulked portion deteriorates, resulting in a failure to secure sufficient airtightness upon exposure to repeated heat cycles. When the hardness difference "H1–H2" between the inner and outer cylindrical members is less than 30, the inner cylindrical member fails to sufficiently receive the caulking force and thus suffers an undesirably intensive deformation, Also, the caulking-related deformation of the outer cylindrical member becomes unsatisfactory. As a result, the caulked portion potentially fails to maintain airtightness. When the Vickers hardness H1 of the inner cylindrical member is less than Hv 250 or the Vickers hardness H2 of the outer cylindrical member is in excess of Hv 330, the thermal shock resistance of the caulked portion deteriorates and the caulked portion fails to maintain sufficient airtightness upon exposure to repeated heat cycles. The reason for this is as follows. When the Vickers hardness H1 of the inner cylindrical member is less than Hv 250, rigidity of the inner cylindrical member becomes insufficient; consequently, conceivably, the inner cylindrical member undergoes undesirably intensive deformation during caulking, resulting in impairment in airtightness. When the Vickers hardness H2 of the outer cylindrical member is in excess of Hv 330, the rigidity of the outer cylindrical member becomes too high; consequently, conceivably, the deformation of the outer cylindrical member becomes unsatisfactory during caulking, or forcible caulking may cause nonuniform deformation or cracking, resulting in impairment in airtightness. Notably, the hardness difference "H1–H2" is more preferably not less than 50.

Preferably, the thickness of the inner cylindrical member is 0.6 mm to 1.0 mm, and the thickness of the outer cylindrical member is 0.2 mm to 0.6 mm. When the inner cylindrical member has a thickness of less than 0.6 mm, even when the hardness H1 of the inner cylindrical member is not less than Hv 250, the inner cylindrical member fails to sufficiently receive the caulking force, potentially resulting in impairment in airtightness of the caulked portion. When the thickness of the inner cylindrical member is in excess of 1.0 mm, caulking may become difficult to perform. When the thickness of the outer cylindrical member is less than 0.2 mm, the outer cylindrical member is apt to deform in association with a lack of strength thereof. When the thickness of the outer cylindrical member is in excess of 0.6 mm, the caulking force fails to be sufficiently exerted on the inner cylindrical member, and thus a sound caulked portion becomes difficult to obtain.

According to the studies conducted by the present inventors, so long as the hardness difference between the inner and outer cylindrical members is not less than 30 (preferably, not less than 50), through employment of a hardness H2 of the outer cylindrical member of at least Hv 160, the caulked portion maintains good thermal shock resistance at a hardness H1 of the internal cylindrical member of up to Hv 430. This indicates that increasing the hardness of the inner cylindrical member results in an expansion of the hardness range of the outer cylindrical member over which a strong caulked portion can be attained. In other words, even when hardness varies among outer cylindrical members due to process-related causes, a strong caulked portion having excellent thermal shock resistance can be readily obtained. Specifically, employment of a hardness H1 of the inner cylindrical member of not less than Hv 300 has the effect of markedly expanding the hardness range of the outer cylindrical member over which a strong caulked portion can be formed, thereby facilitating process control. Accordingly, more preferably, the hardness H1 of the inner cylindrical member assumes a value of not less than Hv 330. The inner and outer cylindrical members may be made of an iron material that can be cold-worked, such as an austenitic steel. The hardness of such material is generally not greater than Hv 430.

When the outer cylindrical member is made of an austenitic stainless steel through cold-working, such as forging, drawing, or deep-drawing, the Vickers hardness H2 thereof is more preferably adjusted to Hv 175 to 275. This is done for the following reason.

Advancement of work hardening often causes a cold-worked member to assume a high hardness of Hv 350 to 400, which is unsuitable for caulking. Before being caulked, the member is desirably annealed at an appropriate temperature so that the hardness thereof falls within a range adequate for caulking. In this case, the hardness of the cold-worked member after annealing does not necessarily vary linearly with annealing temperature. Specifically, the hardness varies with temperature to a relatively small extent until temperature rises to a certain temperature (first temperature region). When the certain temperature is reached, the hardness decreases abruptly within a certain relatively narrow temperature region (second temperature region). In a temperature region (third temperature region) higher than the second temperature region, the hardness again varies with temperature to a relatively small extent.

The Vickers hardness H2 of the outer cylindrical member can be adjusted to the aforementioned range through annealing in the third temperature region or at the high-temperature side of the second temperature region, in which the hardness varies relatively slightly. Annealing within such a temperature region stably imparts to the outer cylindrical member a hardness adequate for caulking even when the annealing temperature varies to some extent. The inner cylindrical member may be adjusted to a hardness of Hv 250 to 430 without undergoing annealing after being cold-worked. Also, through employment of warm working, the outer cylindrical member may be adjusted to a hardness of Hv 160 to 330 without undergoing annealing after being cold-worked, In terms of corrosion resistance, the inner cylindrical member and the outer cylindrical member are preferably made of stainless steel. Examples of such stainless steel include stainless steel as described in JIS G4304; specifically, austenitic stainless steel (stainless steel which shows an austenitic structure at room temperature) such as SUS201; SUS202, SUS301, SUS301J, SUS302, SUS302B, SUS304, SUS304L, SUS304N1, SUS304N2, SUS304LN, SUS305, SUS309S, SUS310S, SUS316, SUS316L, SUS316N, SUS316LN, SUS316J1, SUS316J1L, SUS317, SUS317L, SUS317J1, SUS321, SUS347, or SUSXM15J1; austenitic-ferritic stainless steel (stainless steel which shows a two-phase structure of austenite and ferrite) such as SUS329J1 or SUS329J2L; ferritic stainless steel (stainless steel which, upon undergoing heat treatment, does not harden and shows a ferritic structure) such as SUS405, SUS410L, SUS429, SUS430, SUS430LX, SUS434, SUS436L, SUS444, SUS447J1, or SUSXM27; and precipitation hardening stainless steel (stainless steel which, through addition of, for example, aluminum and copper, can be hardened through precipitation of a compound primarily formed of the elements which is effected by heat treatment) such as SUS631.

The concept of "stainless steel" appearing in the present invention includes the following beat-resisting steel.

(1) Austenitic Heat-resisting Steel

Examples of austenitic heat-resisting steel include steel of a composition specified in, for example, JIS G4311 or G4312; specifically, SUS31, SUH35, SUH36, SUH37, SUH38, SUH309, SUH310, SUH330, SUH660, or SUH661. In the present invention, austenitic heat-resisting steel is included in the concept of the austenitic stainless steel.

(2) Ferritic Heat-resisting Steel

Examples of ferritic heat-resisting steel include steel of a composition specified in, for example, JIS G4311 or G4312; specifically, SUH446. In the present invention, the ferritic heat-resisting steel is included in the concept of the ferritic stainless steel.

(3) Martensitic Heat-resisting Steel

Examples of martensitic heat-resisting steel include steel of a composition specified in, for example, JIS G4311 or G4312; specifically, SUS1, SUS3, SUS4, SUS11, SUS600, or SUS616. In the present invention, the martensitic heat-resisting steel is included in the concept of the martensitic stainless steel.

In terms of workability (particularly cold workability) and hence improvement in manufacturing efficiency for members, ferritic stainless steel and austenitic stainless steel are preferred. In view of the gas sensor being used at high temperature and high humidity, austenitic stainless steel is particularly preferred.

In the overlap zone between the inner cylindrical member and the outer cylindrical member, the outer cylindrical member may be caulked to the inner cylindrical member so as to form an annular main caulked portion along a circumferential direction and a rotation-prevention portion. The rotation-prevention portion is adapted to prevent relative rotation between the inner and outer cylindrical members about their common axis at the main caulked portion. The main caulked portion includes a cylindrical contact surface between the inner and outer cylindrical members, thereby providing excellent airtightness and thus reliably preventing, for example, the entry of water into the interior of the inner cylindrical member. Through formation of the rotation-prevention portion, even when a torsional force about the common axis of the inner and outer cylindrical members is exerted between the inner and outer cylindrical members, relative rotation between the inner and outer cylindrical members is prevented, thereby further reliably establishing airtightness at the caulked portion.

The rotation-prevention portion may assume the form of an auxiliary caulked portion which is located on at least one side of the main caulked portion as viewed in the axial direction of the outer cylindrical member and is formed through caulking of the outer cylindrical member to the inner cylindrical member, The auxiliary caulked portion can be readily formed and yields an excellent rotation-prevention effect. Specifically, the auxiliary caulked portion is located adjacent to and spaced a predetermined distance from the main caulked portion in the axial direction of the outer cylindrical member, and may assume an annular form along the circumference of the outer cylindrical member. Through formation of the annular auxiliary caulked portion adjacent to the main caulked portion, the rotation-prevention effect can be further improved. Further, the auxiliary caulked portion may assume a polygonal transverse cross section. Since the contact faces between the inner and outer cylindrical members define a prismatic form, relative rotation between the inner and outer cylindrical members is prevented even under application of a torsional force.

The auxiliary caulked portion is preferably located closer to the sensing element than is the main caulked portion. Since a tip portion of the gas sensor is often exposed to high temperature, the main caulked portion, which is primarily intended to establish airtightness, is more preferably located away from such a heat source through employment of the above-described arrangement.

The main caulked portion and the auxiliary caulked portion can be simultaneously formed through use of two caulking punch units which each include a plurality of caulking punches for compressing the outer cylindrical member circumferentially from outside and which are spaced a predetermined distance apart in the axial direction of the outer cylindrical member. Since the main caulked portion and the auxiliary caulked portion are simultaneously formed in a single caulking step, this process is not only efficient but also yields the following effect. Through compression by the caulking punches, the outer cylindrical member locally bites and is pressed against the inner cylindrical member, thereby forming the caulked portion. The biting deformation is apt to be accompanied by a wrinkling portion or a lifting portion which is formed on the outer cylindrical member along the pressed portion. If the main caulked portion and the auxiliary caulked portion are formed sequentially, the first caulked portion is affected by a wrinkling portion or a lifting portion associated with the caulked portion formed next, potentially impairing airtightness. However, through simultaneous formation of the main and auxiliary caulked portions as described above, a wrinkling portion or a lifting portion can be confined to within a region located between the main and auxiliary caulked portions, thereby establishing sufficient adhesion or airtightness at both main and auxiliary caulked portions.

In the above-described gas sensor structure, the sensing element may be formed such that the sensing portion thereof includes an oxygen concentration cell element which operates by using as reference gas air introduced into the casing. In this case, the inner cylindrical member serves as a main barrel for accommodating the sensing element, and the outer cylindrical member serves as a cylindrical filter assembly independent of the main barrel. The main barrel and the cylindrical filter assembly are disposed substantially coaxially. The filter assembly is connected to a rear portion of the main barrel while permitting a lead wire from the sensing element to extend rearward of the filter assembly. The filter assembly may include a filter holder and a filter. The filter holder assumes a cylindrical form and is connected to a rear portion of the main barrel substantially coaxially while the interior thereof communicates with the interior of the main barrel. The filter holder has at least one gas inlet hole formed in a wall thereof. The filter is disposed in such a manner as to cover the gas inlet hole(s) formed in the filter holder and functions to permit transmission of gas while blocking transmission of liquid. In this case, air is introduced into the main barrel through the filter and the gas inlet hole(s). Herein, with respect to the axial direction of the oxygen sensing element, the term "front" implies a portion toward a tip end of the oxygen sensing element, and the term "rear" implies a portion away from the tip end.

Tie above-described structure is characterized in that an air-permeable structure including the filter assumes the form of the filter assembly which is independent of the main barrel and is integrally connected to the main barrel, thereby yielding the following effects.

(1) The filter assembly can be assembled independently of, for example, attachment of the oxygen sensing element into the main barrel. Thus, the filter assembly can be assembled quite efficiently without interference caused by, for example, a lead wire of the sensing element.

(2) Since installation of component members into the main barrel and assembling of the filter assembly can be carried out in parallel, productivity is improved drastically. Even when the filter assembly suffers a defect in installation of the filter, if the defect is discovered before the filter assembly is coupled to the main barrel, the defect can be prevented from affecting a gas sensor product, thereby avoiding potential waste of component members.

The filter used in the present invention may be a waterproof, air-permeable, porous resin filter made of fluoroplastic, such as polytetrafluoroethylene. Specifically, such a material for the filter may have a porous fibrous structure (described in, for example, Japanese Patent Publication (kokoku) Nos. 42-13560, 51-18991, 56-45773, and 56-17216, and Japanese Patent Application Laid-Open (kokai) Nos. 58-145735, 59-152825, 3-221541, 7-126428, and 7-196831; for example, Gore-Tex product of Japan Gore-Tex)) obtained by stretching an unfired compact of, for example, polytetrafluoroethylene (hereinafter called PTFE) in at least one axial direction at a heating temperature lower than the melting point of PTFE.

The filter assembly may include a filter holder, a filter, and an auxiliary filter holder. The filter holder is provided coaxially and integrally with the main barrel such that the interior of the filter holder communicates with the interior of a rear portion of the main barrel. The filter holder has at least one gas inlet hole formed in a wall thereof. The filter is disposed around the filter holder in such a manner as to cover the gas inlet hole(s) formed in the filter holder and functions to permit transmission of gas while blocking transmission of liquid. The auxiliary filter holder is formed into a cylindrical shape and is disposed around the filter. The auxiliary filter holder has at least one auxiliary gas inlet hole formed therein and holds the filter in cooperation with the filter holder. In this case, air is introduced into the main barrel through the auxiliary gas inlet hole(s), the filter, and then the gas inlet hole(s). The filter is reliably held between the inner filter holder and the outer auxiliary filter holder and can be easily attached onto the filter holder. For example, when the filter is formed into a cylindrical shape, the filter is fitted onto the filter holder, and then the auxiliary filter holder is fitted onto the filter. Subsequently, a holder coupling portion for coupling the filter holder and the auxiliary filter holder is formed at such a position as not to interfere with the gas inlet hole(s) and the auxiliary gas inlet hole(s).

A plurality of gas inlet holes and auxiliary gas inlet holes may be formed in the filter holder and the auxiliary filter holder, respectively, in such a manner as to be located at axially intermediate portions thereof and be arranged at circumferentially predetermined intervals and at mutually corresponding positions. This arrangement enables air to be uniformly introduced into the main barrel through the filter assembly. A filter of, for example, a cylindrical shape may be disposed around the filter holder, Then, while the filter is held between the filter holder and the auxiliary filter holder, the auxiliary filter holder may be caulked to the filter holder, thereby forming an annular filter-caulking portion along the circumference thereof. The filter-caulking portion serves as the holder coupling portion. Through employment of the filter-caulking portion as the holder coupling portion, assembling work for the filter assembly is further facilitated. The annular filter-caulking portion may be formed on the axially opposite sides of the row of gas inlet holes and auxiliary gas inlet holes, In this case, the filter-caulking portions are formed in such a manner as to hold the corresponding filter edges between the auxiliary filter holder and the filter holder. This minimizes the possibility of formation of a passage which extends from the auxiliary gas inlet holes to the gas inlet holes of the filter holder while bypassing the filter edge, and hence minimizes the possibility of water leaking into the interior of the filter holder and then into the interior of the main barrel through such a potential passage.

When the filter is formed into a cylindrical shape and is disposed around the filter holder as described above, the auxiliary filter holder can be disposed such that the axially rear end thereof is aligned with that of the filter. Thus, the filter-caulking portion can be circumferentially formed along the rear end of the filter. This arrangement enables a worker to visually observe the rear end face of the filter located between the filter holder and the auxiliary filter holder. When the cylindrical filter is fitted onto the filter holder, and then the auxiliary filter holder is axially moved so as to be fitted onto the filter, the filter may move together with the auxiliary filter holder with a resultant dislocation from an intended position. If the filter-caulking portion is formed without correction of the dislocation, the filter is dislocated from the filter-caulking portion, resulting in incomplete seal. However, since a worker can visually observe the rear end face of the filter as described above, any such defect in filter caulking can be easily discovered and corrected accordingly.

When the filter-caulking portion is formed at the front end portion of the auxiliary filter holder, a filter inspection window may be formed in the filter-caulking portion so as to partially expose the filter. Through observation of the filter through the window, a worker can easily judge whether the filter is properly caulked by the filter-caulking portion located at the front end portion of the auxiliary filter holder.

BRIEF DESCRIPTION OF THE DRAWINGS

The accompanying drawings, which are included to provide a further understanding of the invention and are incorporated in and constitute part of this specification, illustrate embodiments of the invention and together with the description, serve to explain the principles of the invention. In the drawings.

FIG. 12 shows an enlarged view of an assembly-coupling caulked portion including an auxiliary caulked portion, sectional view taken along line B—B, and sectional view taken along line C—C;

DETAILED DESCRIPTION OF THE PREFERRED EMBODIMENTS

Figure 1:
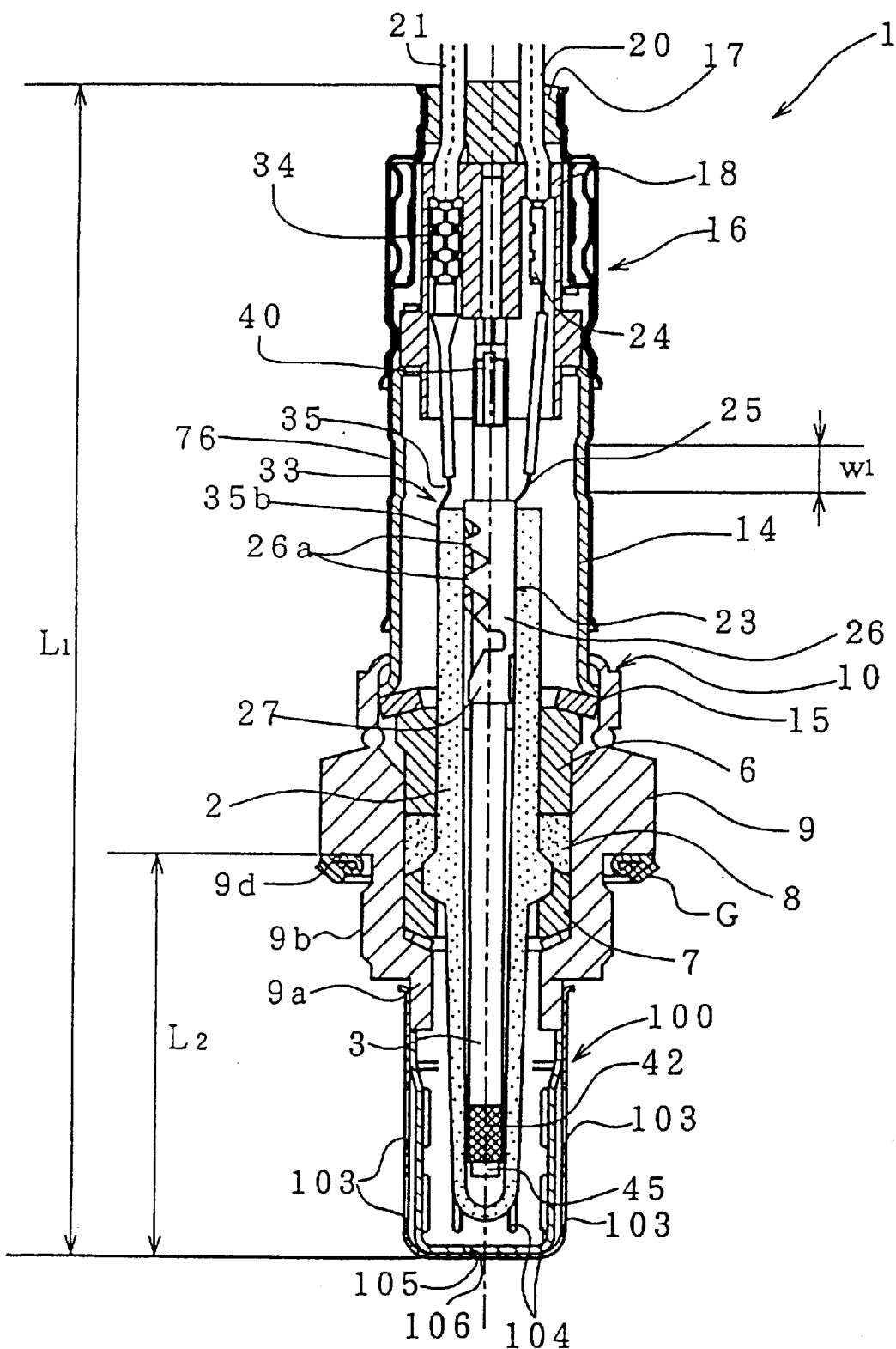
FIG. 1A shows a longitudinal sectional view of an oxygen sensor according to an embodiment of the present invention.

FIG. 1 shows the internal structure of an oxygen sensor according to an embodiment of the present invention. An oxygen sensor 1 shown in FIG. 1 includes an oxygen sensing element 2 and a heating member 3. The oxygen sensing element 2 is a hollow shaft-like member made of oxygen-ion conductive solid electrolyte and having a closed end. The heating member 3 is formed of a shaft-like ceramic heater. A typical example of the solid electrolyte is a solid solution of $ZrO_2$ containing $Y_2O_3$ or CaO. However, a solid solution of $ZrO_2$ and an oxide of an alkaline-earth metal or a rare-ear metal may be used. $HfO_2$ may be contained in $ZrO_2$ as a base.

Figure 2:
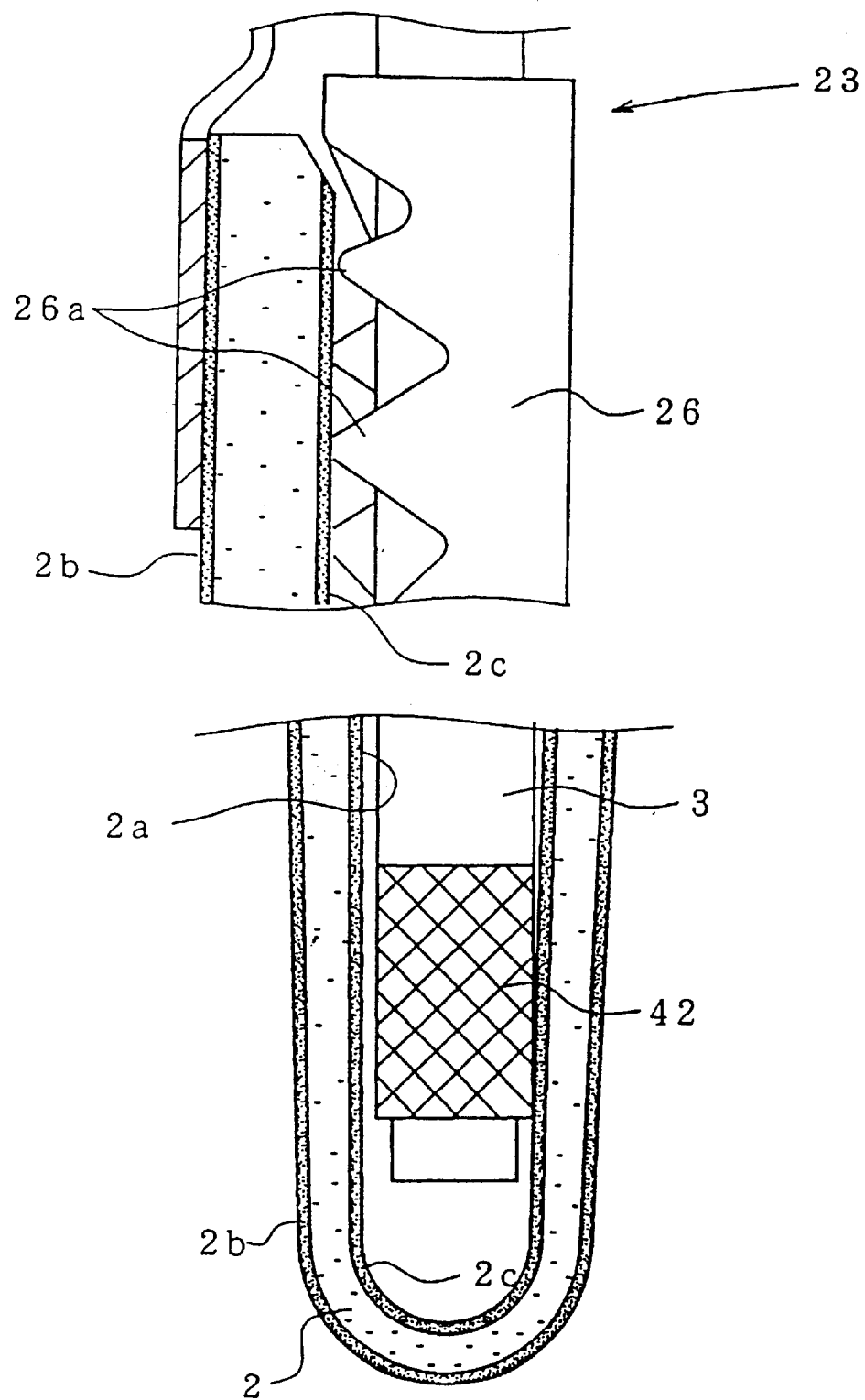
FIG. 2 shows an enlarged sectional view of a sensing portion of the oxygen sensing element of FIG. 1 and a neighboring portion.

The oxygen sensing element 2 is disposed passing through a metallic casing 10 while being electrically insulated from the casing 10. Specifically, the casing 10 is disposed around the middle of the oxygen sensing element 2 and disposed so insulators 6 and 7 of insulating ceramic and a ceramic powdery material 8 of talc are inserted therebetween, The casing 10 includes a metallic shell 9, a main barrel 14 as an inner cylindrical member, and a protector 100. The metallic shell 9 includes a screw portion 9b adapted to mount the oxygen sensor 1 onto an attachment portion, such as an exhaust pipe. The main barrel 14 is connected to one open end portion of the metallic shell 9 such that the interior thereof communicates with that of the metallic shell 9. The protector 100 is connected to the other end portion of the metallic shell 9. As shown in FIG. 2, electrode layers 2b and 2c are layered entirely over the inner and outer surfaces of the oxygen sensing element 2, respectively. The electrode layers 2b and 2c are porous electrodes, for example, Pt porous electrodes, having a reversible catalytic function (oxygen dissociation catalytic function) in relation to a dissociation reaction of oxygen molecules for injecting oxygen into the solid electrolyte of the oxygen sensing element 2 and a recombination reaction of oxygen to cause the solid electrolyte to release oxygen.

Herein, in connection with the axial direction of the oxygen sensing element 2, the term "front" (or "tip") implies a portion at the closed extreme end of the oxygen sensing element 2, and the term "rear" (or "rear end") implies a portion away from the closed extreme end.

A cylindrical protector attachment portion 9a is formed at a front open end portion of the metallic shell 9. The cap-shaped protector 100 is attached onto the protector attachment portion 9a in such a manner as to cover a tip end portion (sensing portion) of the oxygen sensing element 2 with a predetermined space intervening therebetween. A plurality of gas holes 103 to 106 through which exhaust gas passes are formed in the protector 100. The gas holes 103 to 106 enable oxygen in exhaust gas to contact the surface of a tip portion of the oxygen sensing element 2.

The main barrel 14 is fitted to and caulked at the rear open end of the metallic shell 9 in a state that a ring 15 is placed between the main barrel 14 and the insulator 6. A filter assembly 16 has an outer cylindrical member is fitted and fixed to the exterior of the main barrel 14. The upper opening of the filter assembly 16 in FIG. 1 is sealed with a grommet (elastic sealing member) 17 of, for example, rubber. Further, a ceramic separator 18 is located under and adjacent to the grommet 17 within the filter assembly 16. Lead wires 20 and 21 connected to the oxygen sensing element 2 and lead wires (located behind the lead wires 20 and 21 and thus invisible) connected to the heating member 3 are provided passing through the ceramic separator 18 and the grommet 17.

Figure 3:
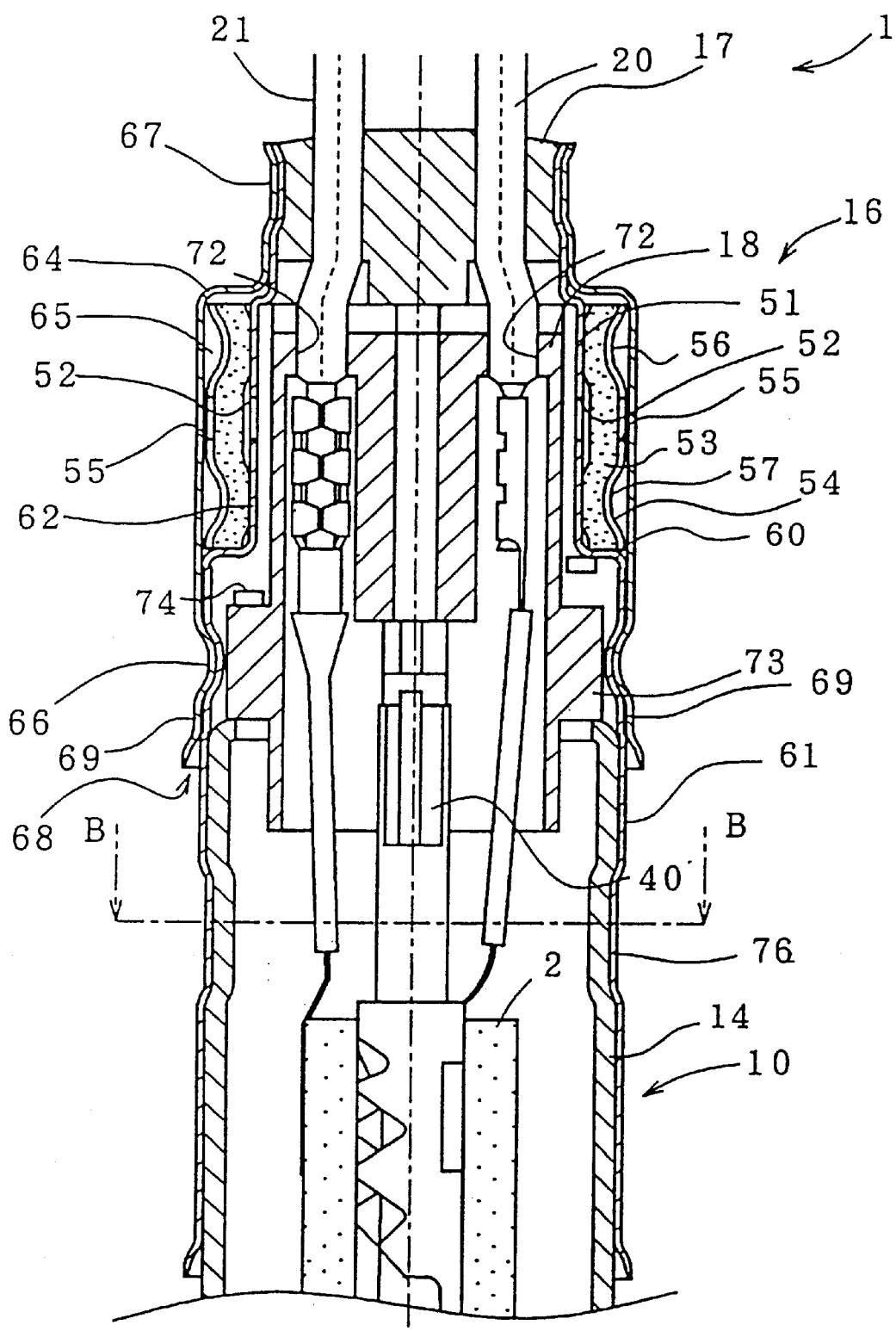
FIG. 3 shows an enlarged sectional view of the filter assembly portion of FIG. 1.

As shown in FIG. 3, a plurality of separator-side lead wire hole 72 extend axially through the ceramic separator 18 so as to allow the lead wires 20 and 21 to pass therethrough. A flange-shaped support portion 73 is projected from the outer surface of the ceramic separator 18 at an axially intermediate position. The ceramic separator 18 is disposed in the following manner. The support portion 73 abuts the rear end face of the main barrel 14, while a portion of the ceramic separator 18 located on the front side with respect to the support portion 73 is inserted into a rear end portion of the main barrel 14. A portion of the ceramic separator IS located on the rear side with respect to the support portion 73 is projected to the exterior of the main barrel 14.

The lead wire 20 is electrically connected to the inner electrode layer 2c (FIG. 2) of the oxygen sensing element 2 through a connector portion 24 of a terminal member 23, a lead-out strip portion 25, and an internal electrode connecting portion 26 of the terminal member 23. The lead wire 21 is electrically connected to the outer electrode layer 2b (FIG. 2) of the oxygen sensing element 2 through a connector portion 34, a lead-out strip portion 35 connected to the connector portion 34, and an external electrode connecting portion 35b of another terminal member 33.

When the exhaust gas temperature is sufficiently high, the oxygen sensing element 2 is heated by the exhaust gas, so that it is activated. When the exhaust gas is at low temperature upon engine startup, for example, the oxygen sensing element 2 is forcibly heated by the heating member 3 to be activated. The heating member 3 is usually a ceramic heater. In the ceramic heater, a ceramic bar 45 made mainly of, for example, alumina is used as a core member. A heating portion 42 is formed on a tip portion of the ceramic bar 45. The heating portion 42 includes a resistor wire part (not shown) patterned in a zigzag fashion, for example. Current is fed to the resistor wire part through a lead wire extending from a heater terminal 40, thereby beating a tip portion (sensing portion) of the oxygen sensing element 2 to a predetermined activation temperature or higher.

The heating member 3 is held within a hollow portion of the oxygen sensing element 2 by means of the terminal member 23. The terminal member 23 includes a heating member holding portion 27 located at the side of the tip of the heating member 3 within respect to the internal electrode connecting portion 26 (i.e., at the near side with respect to the heating portion 42). The heating member holding portion 27 is shaped in a letter C in cross section to surround the heating member 3. The heating member holding portion 27 has an internal diameter slightly smaller than the external diameter of the heating member 3 when the heating member 3 is not inserted thereinto. When the heating member 3 is inserted into the heating member holding portion 27, the internal diameter of the heating member holding portion 27 elastically expands to thereby hold the heating member 3 by means of a frictional force exerted therebetween. In the structure of FIG. 1, the heating member holding portion 27 is provided at only one axial end of the internal electrode connecting portion 26.

In order to form the internal electrode connecting portion 26, a blank sheet portion having saw-tooth contact parts 26a formed at opposite side edges are bent into a cylindrical form, which may surround the heating member 3. The internal electrode connecting portion 26 functions to axially position the heating member 3 within the hollow portion of the oxygen sensing element 2 by means of a frictional force exerted between the outer surface of the heating member 3 and an inner wall 2a of the hollow portion. Electrical connection with the inner electrode layer 2c (FIG. 2) is established by means of tip portions of the contact parts 26a.

As shown in FIG. 3, the filter assembly 16 includes a filter holder 51. The filter holder 51 has a cylindrical form and is substantially coaxially connected to the exterior of a rear portion of the main barrel 14 (casing 10). The interior of the filter holder 51 communicates with that of the main barrel 14. The filter holder 51 has a plurality of gas inlet holes 52 formed in a wall portion thereof. A filter 53 is disposed around the filter holder 51 in such a manner as to cover the gas inlet holes 52. Further, a cylindrical auxiliary filter holder 54 is disposed around the filter 53. The auxiliary filter holder 54 has at least one auxiliary gas inlet hole 55 formed in a wall portion thereof. The auxiliary filter holder 54 holds the filter 53 in cooperation with the filter holder 51. Specifically, the gas inlet holes 52 and the auxiliary gas inlet hole(s) 55 are formed in the filter holder 51 and the auxiliary filter holder 54, respectively, in such a manner as to be located at axially intermediate portions thereof and arranged at circumferentially predetermined intervals and at mutually corresponding positions. The filter 53 is disposed in such a manner as to circumferentially surround the filter holder 51.

The filter 53 is a water-repellent filter of a porous fibrous structure (for example, Gore-Tex (product of Japan Gore-Tex)), Such a porous fibrous structure is obtained by stretching an unfired compact of, for example, polytetrafluoroethylene (hereinafter referred to as PTFE) in at least one axial direction at a heating temperature lower than the melting point of PTFE. The water-repellent filter prevents penetration of liquid which mainly contains water, but permits penetration of gas such as air and/or water vapor. Through employment of the water-repellent filter, air as a reference gas is introduced into the main barrel 14 (casing 10) through the auxiliary gas inlet holes 55, the filter 53, and the gas inlet holes 52, while liquid-phase water is prevented from entering into the main barrel 14.

Figure 4:
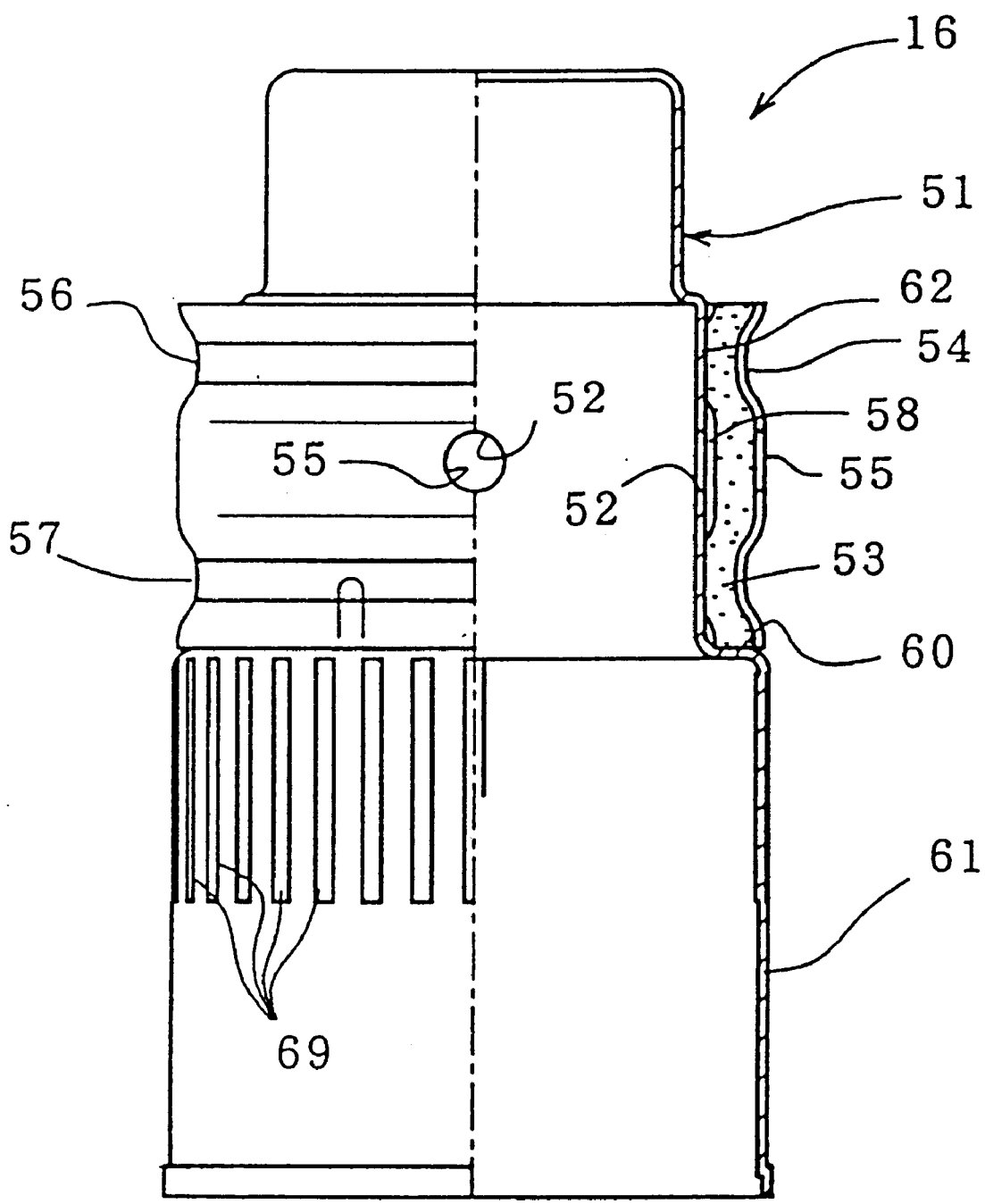
FIG. 4 shows a partially sectional front view of a filter assembly.

As shown in FIG. 4, while the filter 53 is in close contact with the inner surface of the auxiliary filter holder 54, a predetermined gap 58 is annularly formed between the filter 53 and the outer surface of the filter holder 51 along, for example, a row of auxiliary gas inlet holes 55. Further, annular filter-caulking portions 56 and 57 are formed on the auxiliary filter holder 54 at the axially opposite sides of the row of auxiliary gas inlet holes 55. Through formation of the filter-caulking portions 56 and 57, the auxiliary filter holder 54 and the filter holder 51 are coupled together with the filter 53 intervening therebetween.

The filter holder 51 includes a stepped portion 60 formed at an axially intermediate portion thereof; a first portion 61 formed at the axially front side of the stepped portion 60; and a second portion 62 formed at the axially rear side of the stepped portion 60. The diameter of the second portion 62 is smaller than that of the first portion 61. The gas inlet holes 52 are formed in a wall of the second portion 62. The internal diameter of the auxiliary filter holder 54 is smaller than the external diameter of the first portion 61.

Referring back to FIG. 3, the filter holder 51 is disposed in such a manner as to surround the ceramic separator 18 while a projecting portion of the ceramic separator 18 is inserted into the interior of the second portion 62 and such that the stepped portion 60 abuts the support portion 73 of the ceramic separator 18 via a metallic elastic member 74 from opposite the main barrel 14. A tip end portion of the filter holder 51, i.e., the first portion 61, overlaps the main barrel 14 from outside, thereby defining an overlap zone. In the overlap zone, the filter holder 51 is caulked to the main barrel 14, thereby forming an annular assembly-coupling caulked portion 76 (hereinafter referred to simply as the caulked portion 76). Through formation of the caulked portion 76, the filter holder 51 is pressed against and coupled to the main barrel 14 while airtightness is established between the inner surface of the filter holder 51 and the outer surface of the main barrel 14. In FIG. 1, width w1 of the caulked portion 76 can be about 3 mm.

The main barrel 14 (inner cylindrical member) and the filter holder 51 (outer cylindrical member) are made of stainless steel (SUS304L in FIG. 1). The Vickers hardness H1 of the main barrel 14 is Hv 250 to 430, and the Vickers hardness H2 of the filter holder 51 is Hv 160 to 330. The hardness difference "H1–H2" is not less than 30. The thickness of the main barrel 14 is 0.6 mm to 1.0 mm (for example, 0.8 mm in FIG. 1), and the thickness of the filter holder 51 is 0.2 mm to 0.4 mm (for example, 0.3 mm in FIG. 1). Notably, the main barrel 14 and the filter holder 51 are manufactured through cold working, such as forging or deep drawing and then annealed for hardness adjustment before undergoing assembling work.

Figure 5:
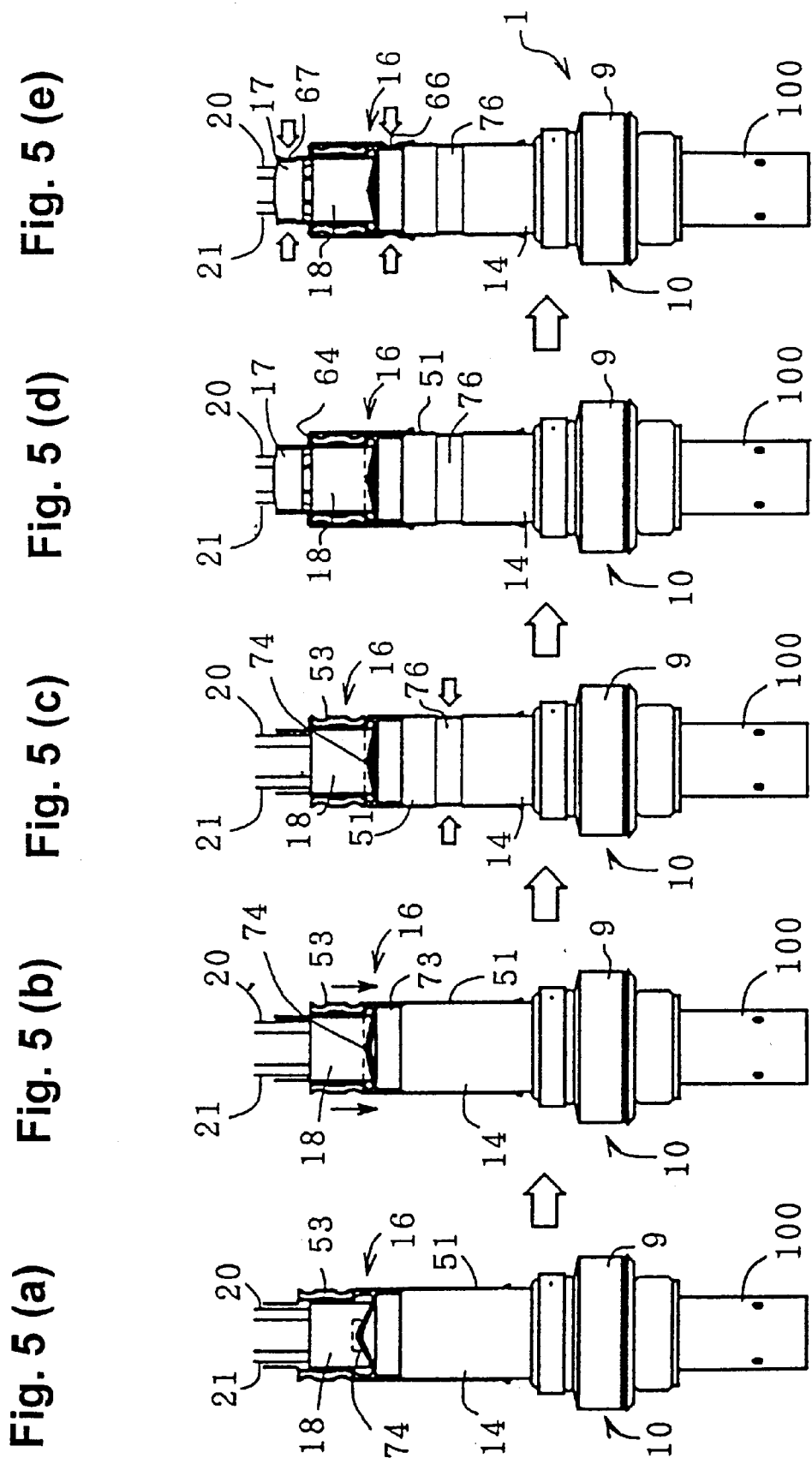
FIGS. 5(a), 5(b), 5(c), 5(d) and 5(e) show views depicting a procedure for assembling the oxygen sensor of FIG. 1.

The filter assembly 16 is coupled to the main barrel 14 according to the following procedure. As shown in FIG. 5(a), the metallic elastic member 74 is fitted onto the ceramic separator 18. Further, a front end portion of the ceramic separator 18 is inserted into the main barrel 14. The filter assembly 16 is previously assembled as shown in FIG. 4. As shown in FIG. 5(a), the filter assembly 16 is attached such that the filter holder 51 surrounds the ceramic separator 18 and the main barrel 14. Notably, the oxygen sensing element 2 and the heating member 3 (FIG. 1), for example, are previously installed within the main barrel 14. The lead wires (only lead wires 20 and 21 of four lead wires are illustrated) from the oxygen sensing element 2 and the heating member 3 are passed through the lead wire holes 72 (FIG. 3) formed in the ceramic separator 18 and left extending outward from a rear open end of the filter holder 51.

Subsequently, as shown in FIG. 5(b), an axial compression force is applied to the main barrel 14 and the filter assembly 16. As a result, the metallic elastic member 74 is compressed and deformed between the filter holder 51 and the support portion 73 of the ceramic separator 18 thereby inducing a force to grip the ceramic separator 18 between the main barrel 14 and the filter holder 51. While this state is maintained, the caulked portion 76 is formed in order to couple the filter holder 51 and the main barrel 14 together as shown in FIG. 5(c). Next, as shown in FIG. 5(d), the elastic sealing member 17 is fitted into the rear open end portion of the filter holder 51. Further, a protection cover 64 is attached onto the filter assembly 16. As shown in FIG. 5(e), caulked portions 66 and 67 are formed, thus completing the assembling work.

Figure 6:
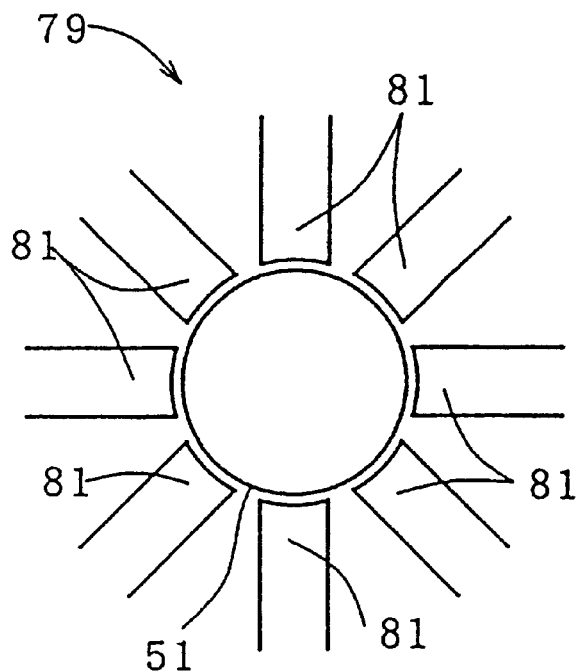
FIGS. 6(a) and 6(b) show a conceptual view of a caulker.
Figure 6:
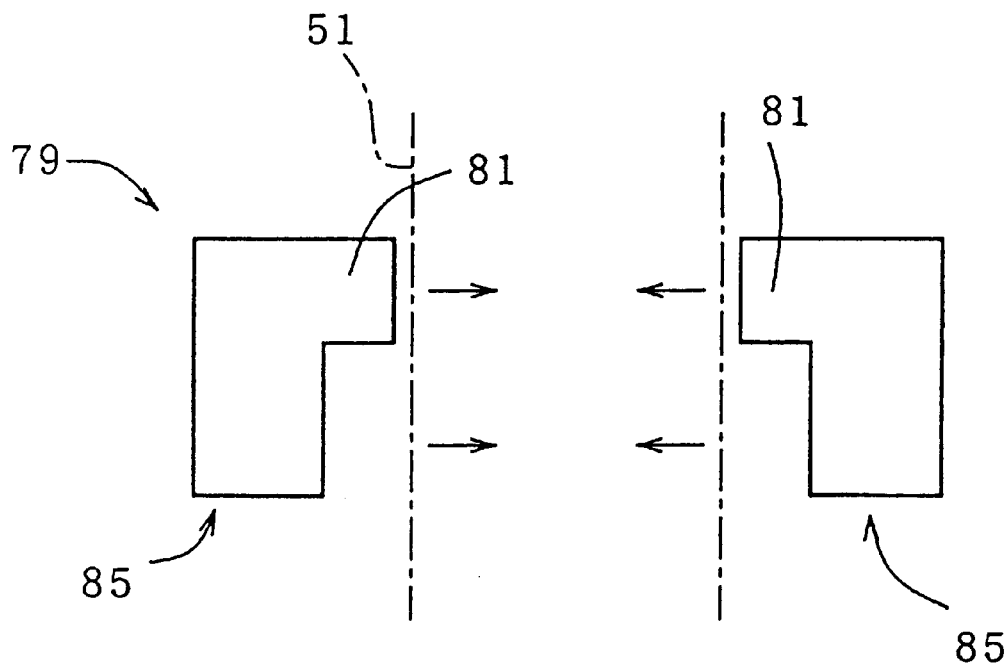

The caulked portion 76 can be formed by use of, for example, a caulker 79 as conceptually shown in FIG. 6. As shown in FIG. 6(a), the caulker 79 includes a plurality of caulking punches 81 for circumferentially compressing the filter holder 51 from outside. End surfaces of the caulking punches 81 are arranged in such a manner as to define a cylindrical surface. As shown in FIG. 6(b), the caulking punches 81 are adapted to radially move toward or away from the outer wall surface of the filter holder 51 in unison.

Figure 7:
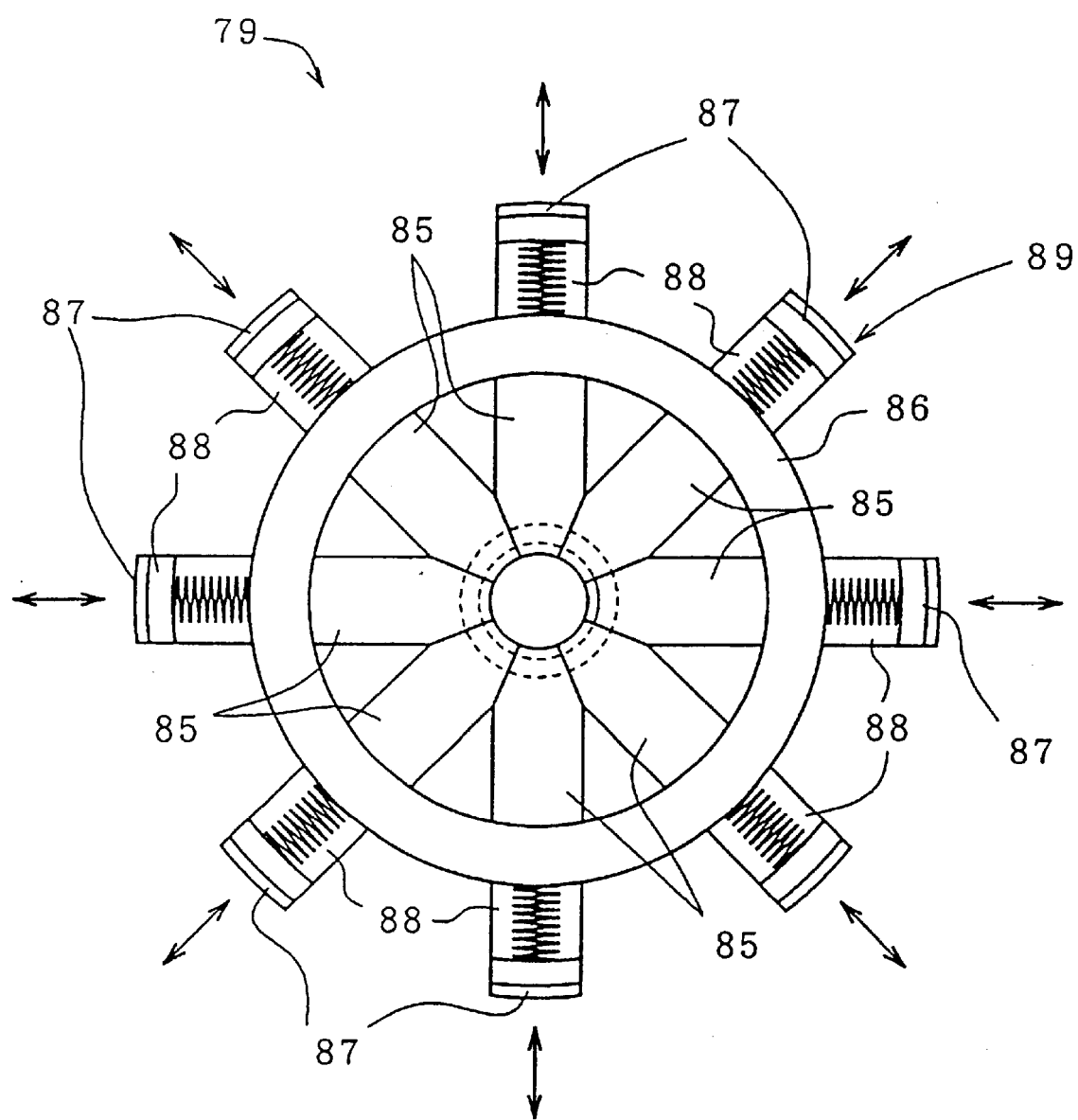
FIG. 7 shows a schematic plan view of a main portion of the caulker of FIGS. 6(a) and 6(b)
Figure 8:
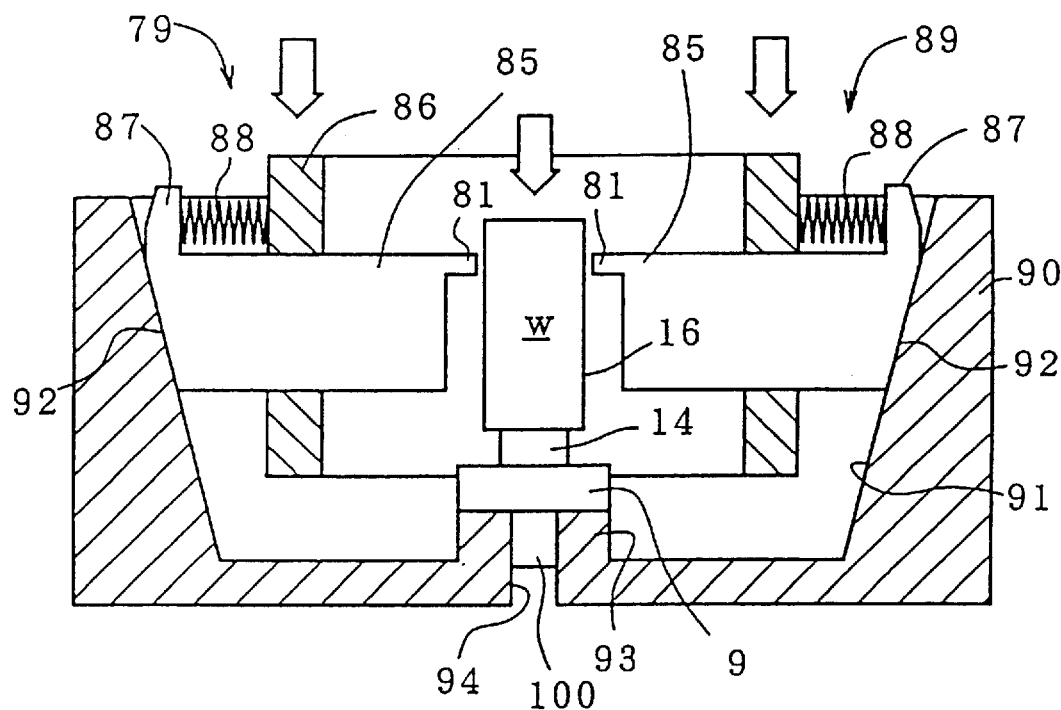
FIGS. 8(a) and 8(b) show a schematic sectional side view showing the main portion of the caulker of FIG. 7.
Figure 8:
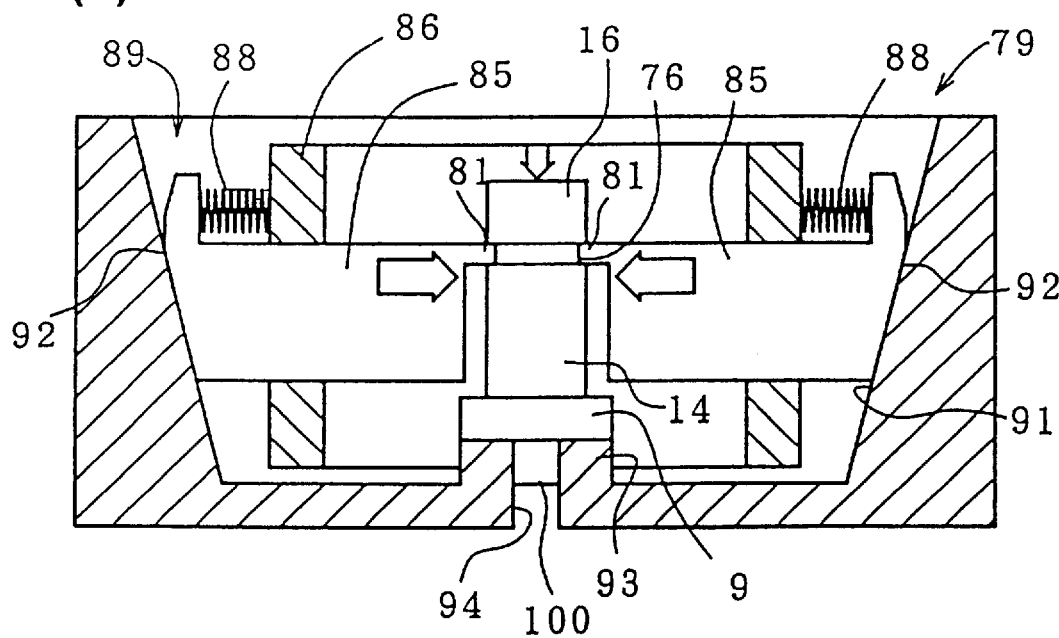

FIG. 7 is a plan view showing an example of the configuration of the caulker 79. The caulker 79 includes a punch assembly 89, which, in turn, includes a punch holder 86 of ring shape and a plurality of punch segments 85. The punch segments 85 are circumferentially arranged on the punch holder 86 and extend through the punch holder 86 in a radially reciprocative manner. A spring support 87 is formed at a rear end portion of each punch segment 85. A spring member 88 is disposed between the spring support 87 and the outer circumferential surface of the punch holder 86 and urges the corresponding punch segment 85 outward. As shown in FIG. 8(a), the caulker 79 further includes a receive unit 90 which cooperatively works with the punch assembly 89. An inner wall 91 of the receive unit 90 is tapered such that a diameter defined by the inner wall 91 reduces toward the bottom of the receive unit 90. A positioning projection 93 is formed at the center of the bottom and has a workpiece insertion hole 94 formed therein.

A workpiece W with the filter assembly 16 coupled to the main barrel 14 is set on the positioning projection 93 such that the protector 100 is inserted into the workpiece insertion hole 94. The metallic shell 9 is supported on the top face of the positioning projection 93, so that the workpiece W is held upright at the center of the bottom of the receive unit 90. The punch assembly 89 is coaxially set within the receive unit 90, so that the punch segments 85 surround the workpiece W. An outer end surface 92 of each punch segment 85 is tapered so as to correspond to the inner wall 91 of the receive unit 90.

In this state, the filter assembly 16 is pressed toward the main barrel 14 by means of an unillustrated pressing mechanism (FIG. 5(b)), and the punch assembly 89 is pressed downward toward the bottom of the receive unit 90. As a result, as shown in FIG. 8(b), because of cam action induced between the tapered outer end surfaces 92 and the inner wall 91, the punch segments 85 approach the workpiece W in unison and are accompanied by compression of the corresponding springs 88. Thus the caulked portion 76 is formed.

The cylindrical protection cover 64 is provided in such a manner as to surround the auxiliary filter holder 51. The protection cover 64 functions to prevent or suppress a direct splash of liquid droplets or adhesion of foreign matter, such as oil or dirt, onto the filter 53. The protection cover 64 is disposed, for example, such that a gas residence space 65 is formed between the protection cover 64 and the filter 53 at a position corresponding to the gas inlet holes 52 (or the auxiliary gas inlet holes 55). The caulked portions 66 and 67 are formed on axially opposite sides of the row of gas inlet holes 52 so as to join the protection cover 64 to the outer surface of the filter holder 51. At a position corresponding to the axially front caulked portion 66, an external communication portion 68 is defined by the protection cover 64 and the filter holder 51 in order to establish communication between the gas residence space 65 and the exterior of the filter assembly 16 for introduction of air into the filter assembly 16.

Figure 9:
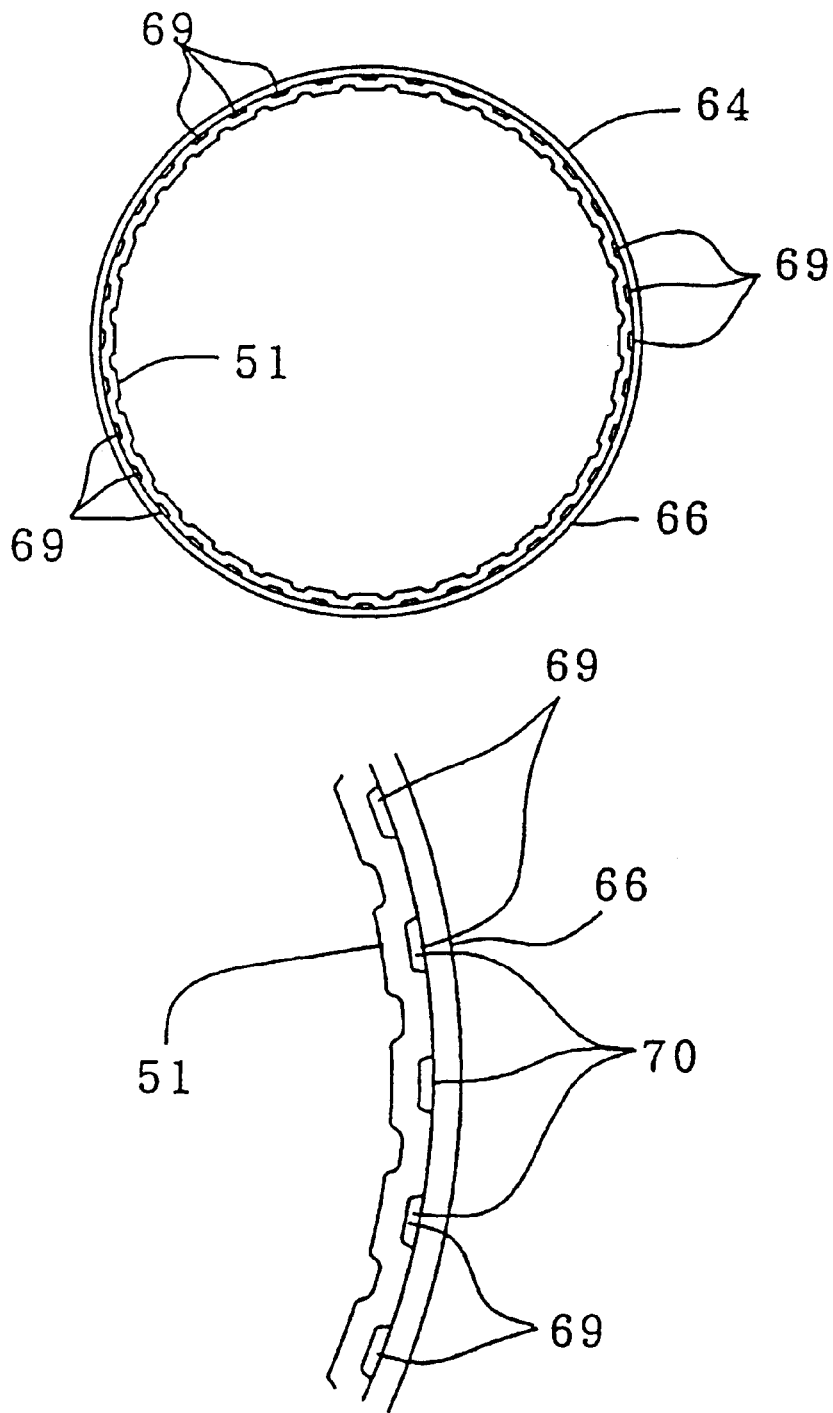
FIG. 9 shows a sectional plan view of a caulked portion of a filter assembly and a protection cover and an enlarged view showing the caulked portion.
Figure 10:
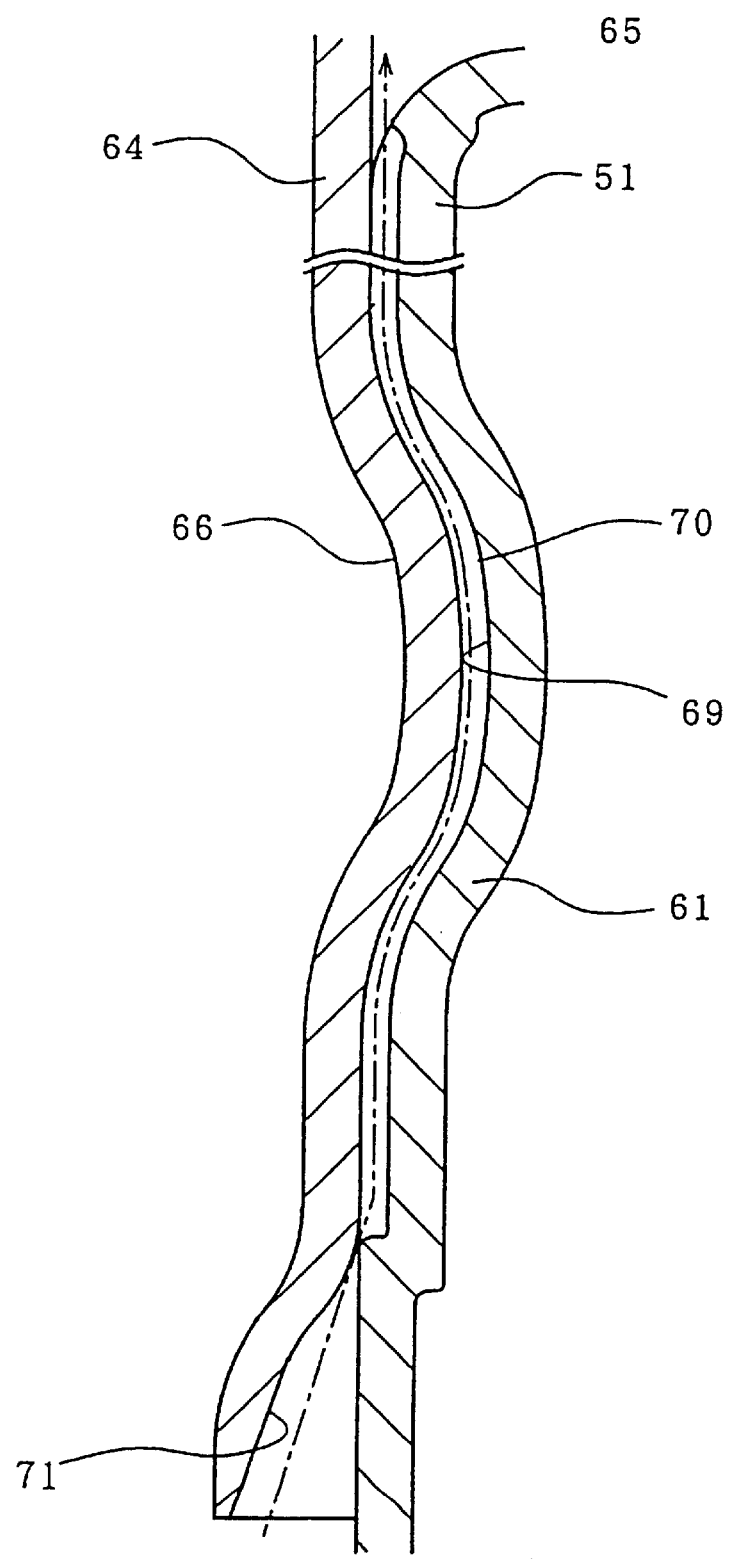
FIG. 10 shows a partially enlarged longitudinal sectional view of the caulked portion of FIG. 9.

As shown in FIG. 4, a plurality groove portions 69 extending in the axial direction of the filter holder 51 are formed on the outer surface of the first portion 61 of the filter holder 51 in such a manner as to be circumferentially arranged at predetermined intervals, These groove portions constitute the external communication portion. As shown in FIGS. 9 and 10, through caulking of the protection cover 64 to the first portion 61 of the filter holder 51, the caulked portion 66 is annularly formed in such a manner as to cross the groove portions 69 and such that gaps 70 remain between the protection cover 64 and the first portion 61 and at the respective bottom portions of the groove portions 69. In this structure, as shown in FIG. 10, in a region defined by the protection cover 64 and the first portion 61 of the filter holder 51, air is introduced into the gas residence space 65 through a front open end portion 71 located at the front side of the gaps 70 formed in the groove portions 69 and then the gaps 70. The caulked portion 67 is formed at a rear end portion of the second portion 62. The caulked portion 66 is formed in such a manner as to face the outer surface of the support portion 73 of the ceramic separator 18. This enables the support portion 73 to receive a compressive force associated with caulking work, so that the caulked portion 66 can be reliably formed.

Operation of the oxygen sensor 1 is described next.

In the thus-constructed oxygen sensor 1 of FIG. 1, air as reference gas is introduced thereinto through the filter 53 of the filter assembly 16. Exhaust gas is introduced through the gas holes 103 to 106 formed in the protector 100 and comes in contact with the outer surface of the oxygen sensing element 2. As a result, an electromotive force is generated in the oxygen sensing element 2 by oxygen concentration cell effect. The generated electromotive force depends on the oxygen concentration difference between the interior and the exterior of the oxygen sensing element 2. The electromotive force is lead out through the lead wires 20 and 21 from the electrode layers 2b and 2c, in the form of a detection signal representative of the oxygen concentration contained in the exhaust gas, thereby determining the oxygen concentration in the exhaust gas.

By setting the hardness H1 of the main barrel 14 and the hardness H2 of the filter holder 51 to the aforementioned values, the caulked portion 76 is improved in airtightness (sealing property) and high-temperature endurance. As a result, even when exposed to, for example, repeated thermal shocks, the caulked portion 76 hardly loosens. Thus, even when water, for example, splashes the caulked portion 76, the caulked portion 76 effectively prevents entry of water into the main barrel 14. This effect is conceivably yielded in the following mechanism. By increasing the Vickers hardness of the filter holder 51 to not less than 160, an obtained hardness of the caulked portion 76 is increased, thereby suppressing the deformation of the caulked portion 76 caused by thermal stress induced therein during exposure to heat cycles and thus preventing the caulked portion 76 from loosening with a resultant improvement in airtightness.

In this case, the Vickers hardness H1 of the main barrel 14 is adjusted to not less than Hv 300, and the hardness difference between the main barrel 14 and the filter holder 51 is set to not less than 50. Thus, when the filter holder 51 having the above high hardness is caulked onto the main barrel 14, the main barrel 14 can sufficiently receive the caulking force, whereby the caulked portion 76 can attain far stronger adhesion.

The above-described structure of the oxygen sensor 1 yields the following effects. The filter assembly can be assembled independently of, for example, attachment of the oxygen sensing element 2 into the casing 10. Thus, the filter assembly 16 can be assembled quite efficiently without interference caused by, for example, lead wires. Also, since installation of component members into the casing 10 and assembling of the filter assembly 16 can be carried out in parallel, productivity is improved drastically. Even when the filter assembly 16 suffers a defect in installation of the filter 53, if the defect is discovered before the filter assembly 16 is coupled to the casing 10, the defect can be prevented from affecting a gas sensor product, thereby avoiding potential waste of component members.

Figure 11:
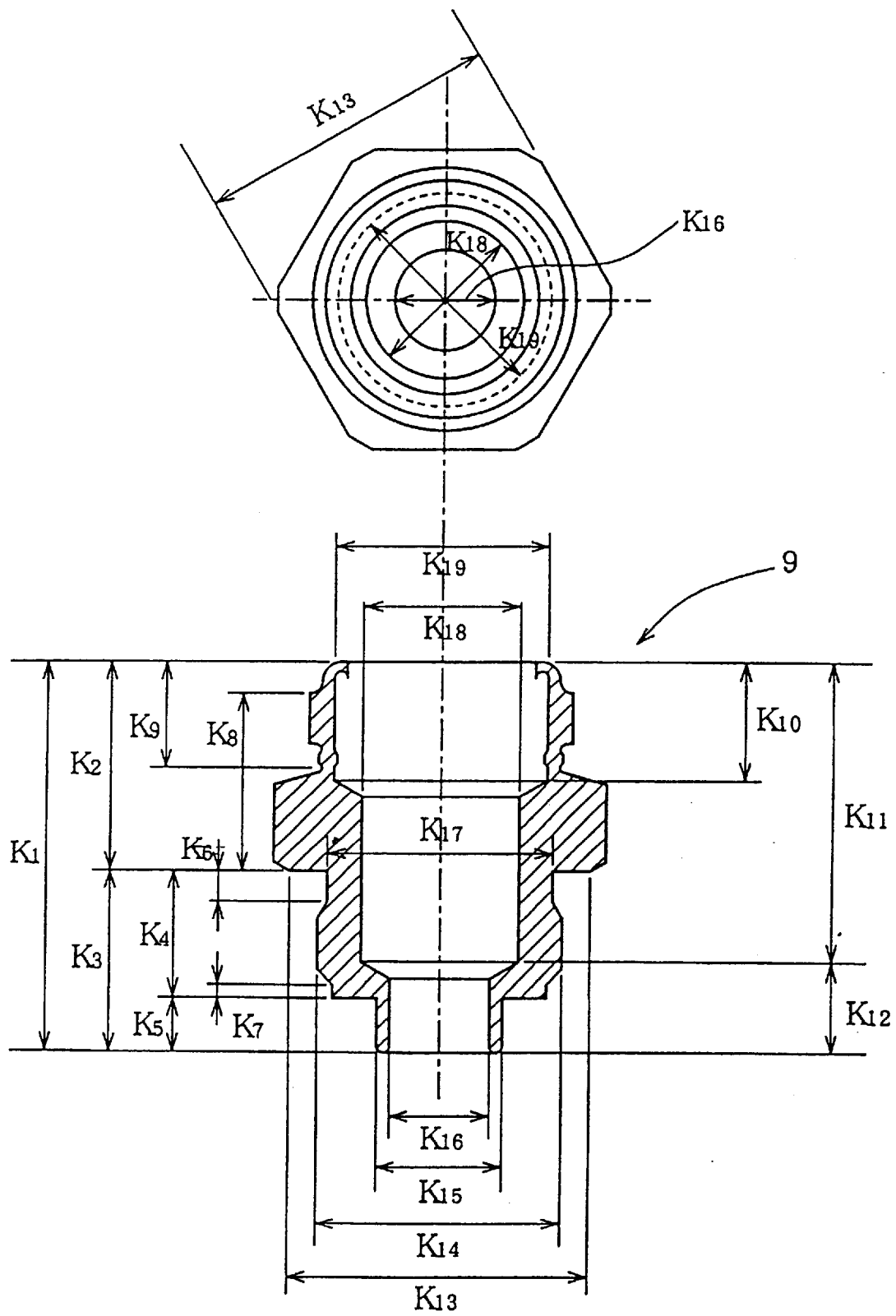
FIG. 11 shows an explanatory view of dimensions of a metallic shell.

Dimensions of the metallic shell 9 shown in FIG. 11 can be set, for example, as follows. K1: 27.6 mm; K2: 14.8 mm; K3: 12.8 mm; K4: 9 mm; K5: 3.8 mm; K6: 2 mm; K7: 1 mm; K8: 11.9 mm; K9: 8.6 mm; K10: 9 mm; K11: 21.1 mm; K12: 6.5 mm; K13: 22 mm diameter; K14: 16.88 mm diameter; K15: 9.48 mm diameter; K16: 7.5 mm diameter, K17: 16.5 mm diameter; K18: 11.6 mm diameter; and K19: 16 mm diameter.

In FIG. 1, the overall length L1 of the oxygen sensor 1 is about 75 mm; and the length L2 between a seat surface 9$d$ for gasket G of the metallic shell 9 and the tip face of the protector 100 is about 29 mm, The bore diameter of the main barrel 14 is about 14.2 mm.

As shown in FIG. 12, the assembly-coupling caulked portion 75 may assume a double caulked form which includes the caulked portion 76 as a main caulked portion and the auxiliary caulked portion 77 as a rotation-prevention portion. The auxiliary caulked portion 77 is located closer to the tip of the oxygen sensing element 2 than is the main caulked portion 76, and has polygonal transverse cross section (octagonal transverse cross section in the present embodiment). This structural feature yields the following effect. The main caulked portion 76 includes a cylindrical contact surface between the main barrel 14 and the filter holder 51, thereby providing excellent airtightness and thus reliably preventing, for example, is water from entering the interior of the main barrel 14. However, as schematically shown in FIG. 14(*b*), when, due to, for example, impact, a strong torsional force is externally exerted on the main barrel 14 and the filter holder 51, the cylindrical contact surface may involve relative rotation between the main barrel 14 and the filter holder 51, potentially resulting in damage to airtightness.

Figure 14:
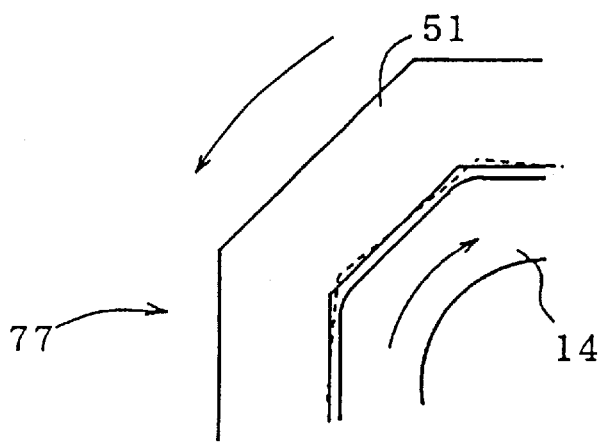
FIGS. 14(a) and 14(b) show an explanatory view depicting actions of a caulked portion and an auxiliary calked portion in an assembly-coupling caulked portion.
Figure 14:
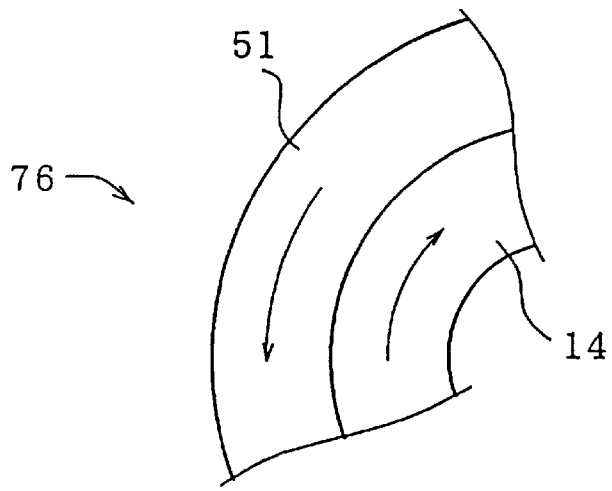

Through employment of the auxiliary caulked portion 77, the contact surface assumes a polygonal transverse cross section as shown in FIG. 14(*a*). Thus, relative rotation between the main barrel 14 and the filter holder 51 is prevented even under application of a torsional force as described above. As a result, even in the main caulked portion 76, such relative rotation can be effectively prevented, thereby further ensuring airtightness between the main barrel 14 and the filter holder 51. The main caulked portion 76 and the auxiliary caulked portion 77 may be reversed in terms of axial position. However, since a tip portion of the oxygen sensor 1 is often exposed to high temperature, the main caulked portion 76, which is primarily intended to establish airtightness, is more preferably located away from such a heat source through employment of the above arrangement.

Figure 13:
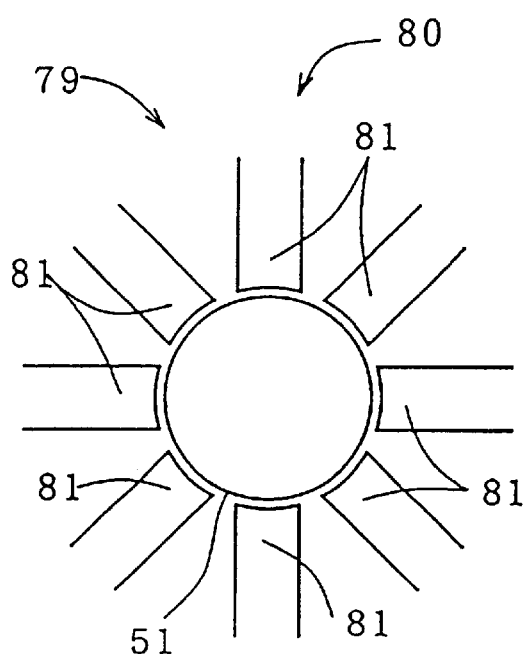
FIGS. 13(a), 13(b) and 13(c) show a conceptual view of a caulker.
Figure 13:
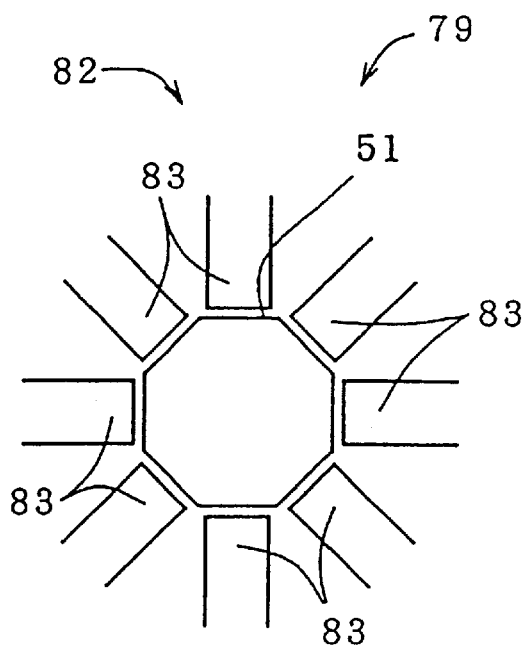
Figure 13:
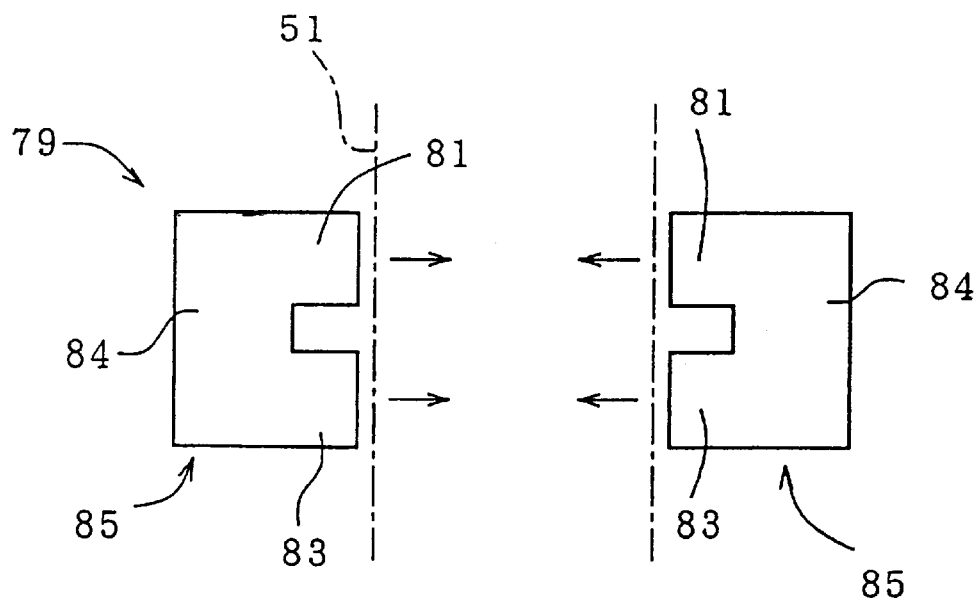

The assembly-coupling caulked portion 75 can be formed by use of, for example, a caulker 79 as conceptually shown in FIG. 13. As shown in FIGS. 13(*a*) and 13(*b*), the caulker 79 includes a plurality of caulking punches 81 and 83 for circumferentially compressing the filter holder 51 from outside. As shown in FIG. 13(*c*), the caulker 79 includes a first caulking punch unit 80 and a second caulking punch unit 82 which are apart from each other a predetermined distance in the axial direction of the filter holder 51. The first caulking punch unit 80 is adapted to form the main caulked portion 76, and end surfaces of the caulking punches 81 are arranged in such a manner as to define a cylindrical surface. The second caulking punch unit 82 is adapted to form the auxiliary caulked portion 77, and end surfaces of the caulking punches 83 are arranged in such a manner as to define an octagonal prismatic surface. As shown in FIG. 13(*c*), the corresponding caulking punches 81 and 83 are connected by means of a connecting portion 84 to thereby form a punch segment 85. Thus, the caulking punches 81 and 83 are adapted to radially move toward or away from the outer wall surface of the filter holder 51 in an integral manner.

By moving the punch segments 85 arranged around the filter holder 51 toward the filter holder 51 in unison, the main caulked portion 76 and the auxiliary caulked portion 77 are concurrently formed on the filter holder 51. Since the main caulked portion 76 and the auxiliary caulked portion 77 are simultaneously formed in a single caulking step, this process not only is efficient but also yields the following effect. Through compression by the caulking punches, the filter holder 51 locally bites and is pressed against the main barrel, thereby forming a caulked portion. The biting deformation is apt to be accompanied by a wrinkling portion or a lifting portion which is formed on the filter holder 51 along the pressed portion. If the main caulked portion 76 and the auxiliary caulked portion 77 are sequentially formed, the first caulked portion is affected by a wrinkling portion or a lifting portion associated with the next caulked portion, potentially impairing airtightness. However, through simultaneous formation of the main caulked portion 76 and the auxiliary caulked portion 77 as described above, a wrinkling portion or a lifting portion can be confined to within a region located between the main caulked portion 76 and the auxiliary caulked portion 77, thereby attaining sufficient adhesion or airtightness at both the main and auxiliary caulked portions 76 and 77.

Figure 15:
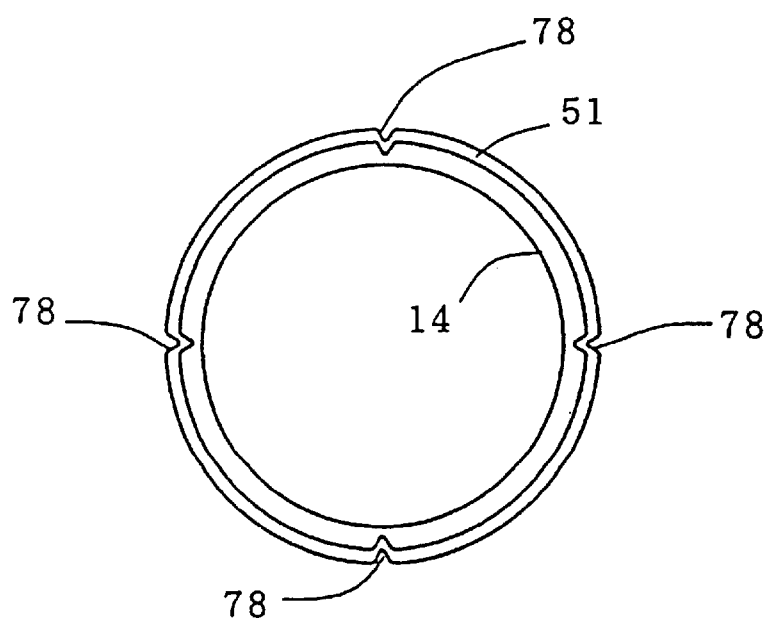
FIG. 15 shows a sectional plan view of a modified embodiment of a rotation-prevention portion.

FIG. 15 shows another embodiment of the rotation-prevention portion. Specifically, the filter holder 51 is notched toward the main barrel 14 such that notches 78 are circumferentially formed and arranged at predetermined intervals.

The sensor structure according to the present invention as described above is also applicable to gas sensor for detecting gas other than oxygen such as an HC sensor or NOx sensor.

EXAMPLES

In order to confirm the effects of the present invention, the following experiments were carried out.

Figure 16:
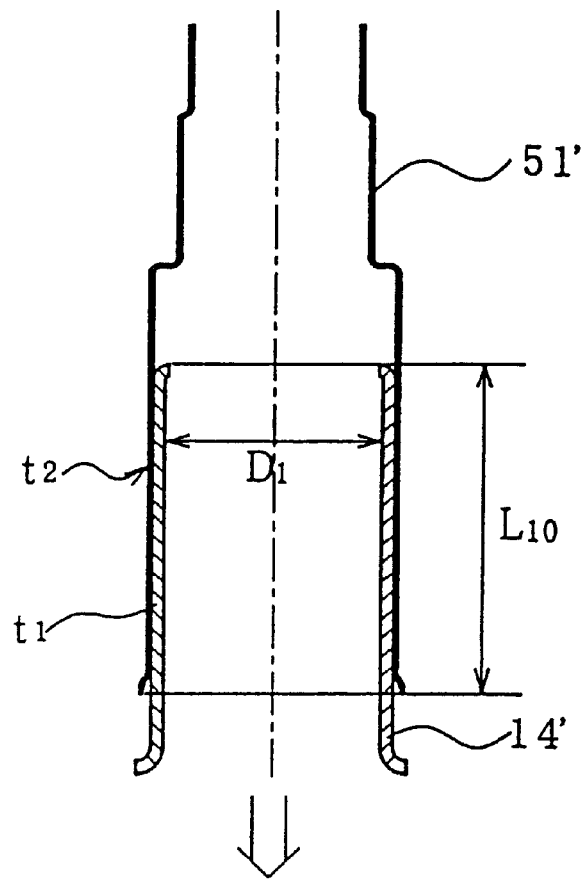
FIGS. 16(a) and 16(b) show an explanatory view of a manufacturing procedure for a test assembly used in experiments on the embodiment.
Figure 16:
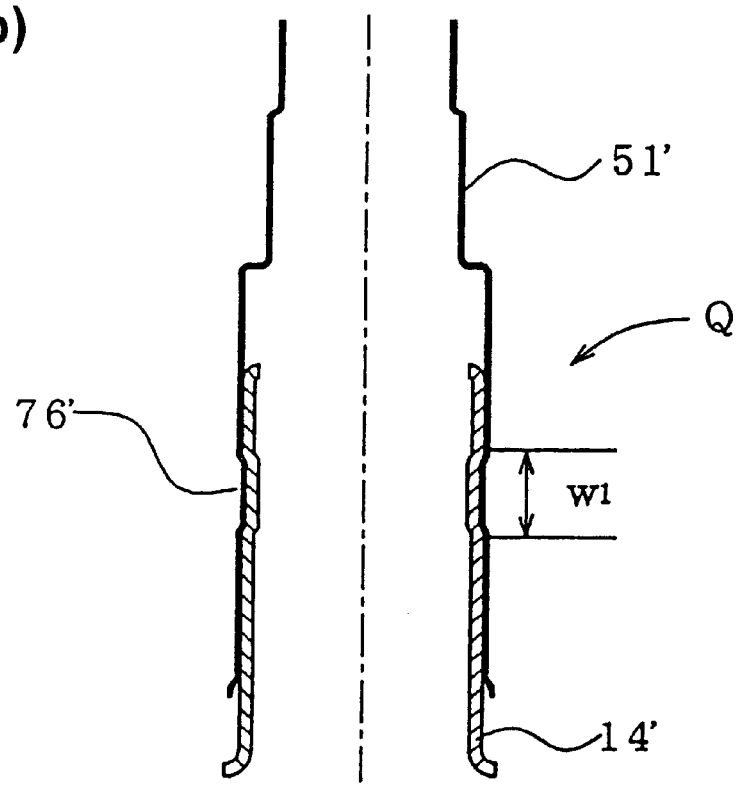

An inner cylindrical member 14' and an outer cylindrical member 51' as shown in FIG. 16(*a*) were prepared as required for the experiment (holes corresponding to the gas inlet holes 52 of, for example, FIG. 3 are not formed in the outer cylindrical member 51'). The inner cylindrical member 14' and the outer cylindrical member 51' had dimensions similar to those of the main barrel 14 and the is filter holder 51 of the sensor 1 of FIG. 1 and were manufactured of stainless steel (SUS304L) similar to that of the main barrel 14 and filter holder 51, through cold working. The Vickers hardness H1 of the inner cylindrical member 14' and the Vickers hardness H2 of the outer cylindrical member 51' (which later becomes the filter holder 51) are on average Hv 400 (range: Hv 375 to 425) as measured at a position where a caulked portion 76', which will be described later, is to be formed.

Figure 18:
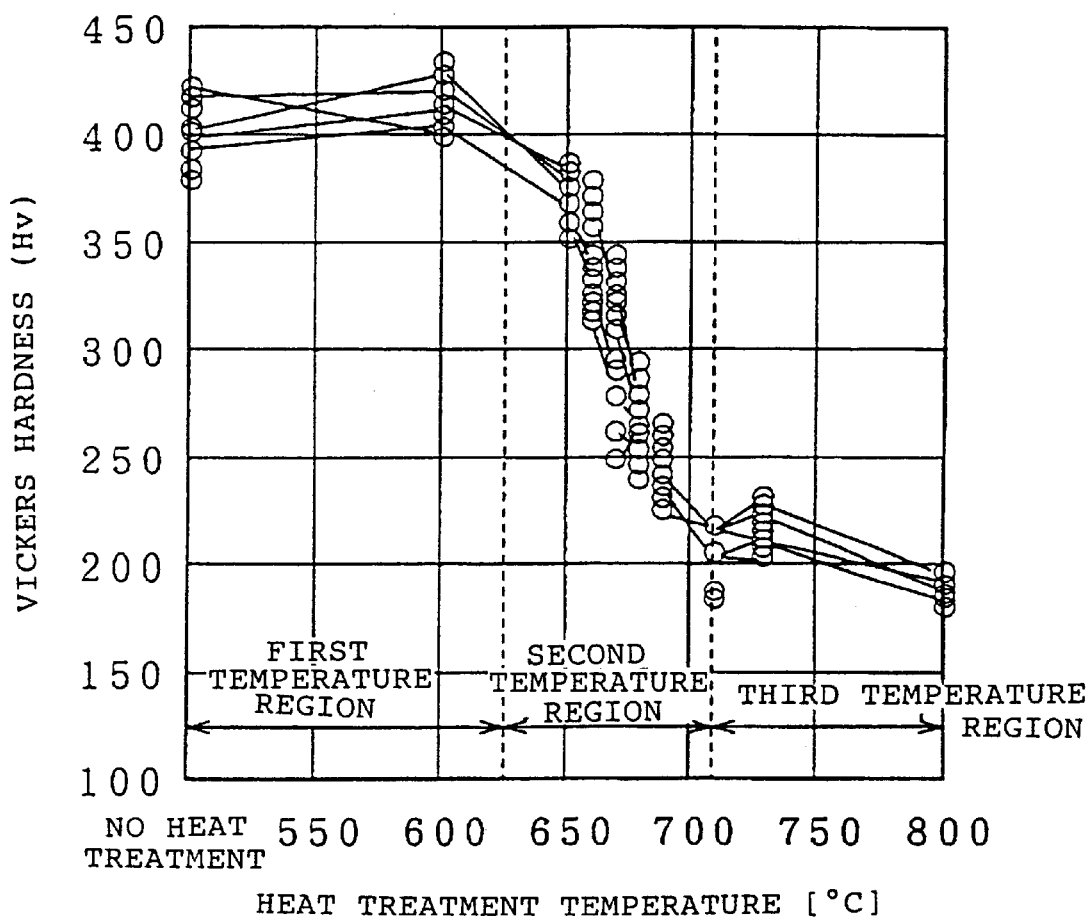
FIG. 18 is a graph showing the relationship between annealing temperature or inner cylindrical members and the Vickers hardness of the anneals cylindrical embers.

The inner cylindrical members 14' and the outer cylindrical members 51' were annealed at various temperatures of 550° C. to 800° C. for 60 minutes in a nitrogen atmosphere so as to adjust H1 to various values of Hv 130 to 410 and H2 to various values of Hv 130 to 400. FIG. 18 shows the relationship between heat treatment temperature and the hardness H1 as measured after heat treatment with respect to the inner cylindrical members 14'. The hardness of the annealed members does not vary linearly with annealing temperature. Specifically, hardness varies to a relatively small extent with temperature until temperature rises to about 620° C. (first temperature region). When the temperature of about 620° C. is reached, hardness reduces abruptly in a relatively narrow temperature region ranging from about 620° C. to about 700° C. (second temperature region). When the temperature further increases in excess of about 700° C. (third temperature region), hardness again varies slightly with temperature.

The obtained inner cylindrical members 14' of various hardness values and the outer cylindrical members 51' of various hardness values were combined such that each of the inner cylindrical members 14' is axially inserted into the corresponding outer cylindrical member 51' as shown in FIG. 16(a), thereby forming an overlap zone as in the case of FIG. 1. An axial length L10 of the overlap zone is not less than 8 mm; a bore diameter D1 of the inner cylindrical member 14' as measured in the overlap zone is 12.2 mm; and a thickness t1 of the inner cylindrical member 14' is 0.8 mm A thickness t2 of the outer cylindrical member 51' is 0.3 mm. As shown in FIG. 16(b), the caulked portion 76' as in the case of the sensor of FIG. 1 was formed in the overlap zone by use of a caulker similar to that of FIGS. 7 and 8, thus manufacturing test assemblies Q. The caulking force was not less than 11 ton, and a width w1 of the caulked portion 76' was about 3 mm.

Figure 17:
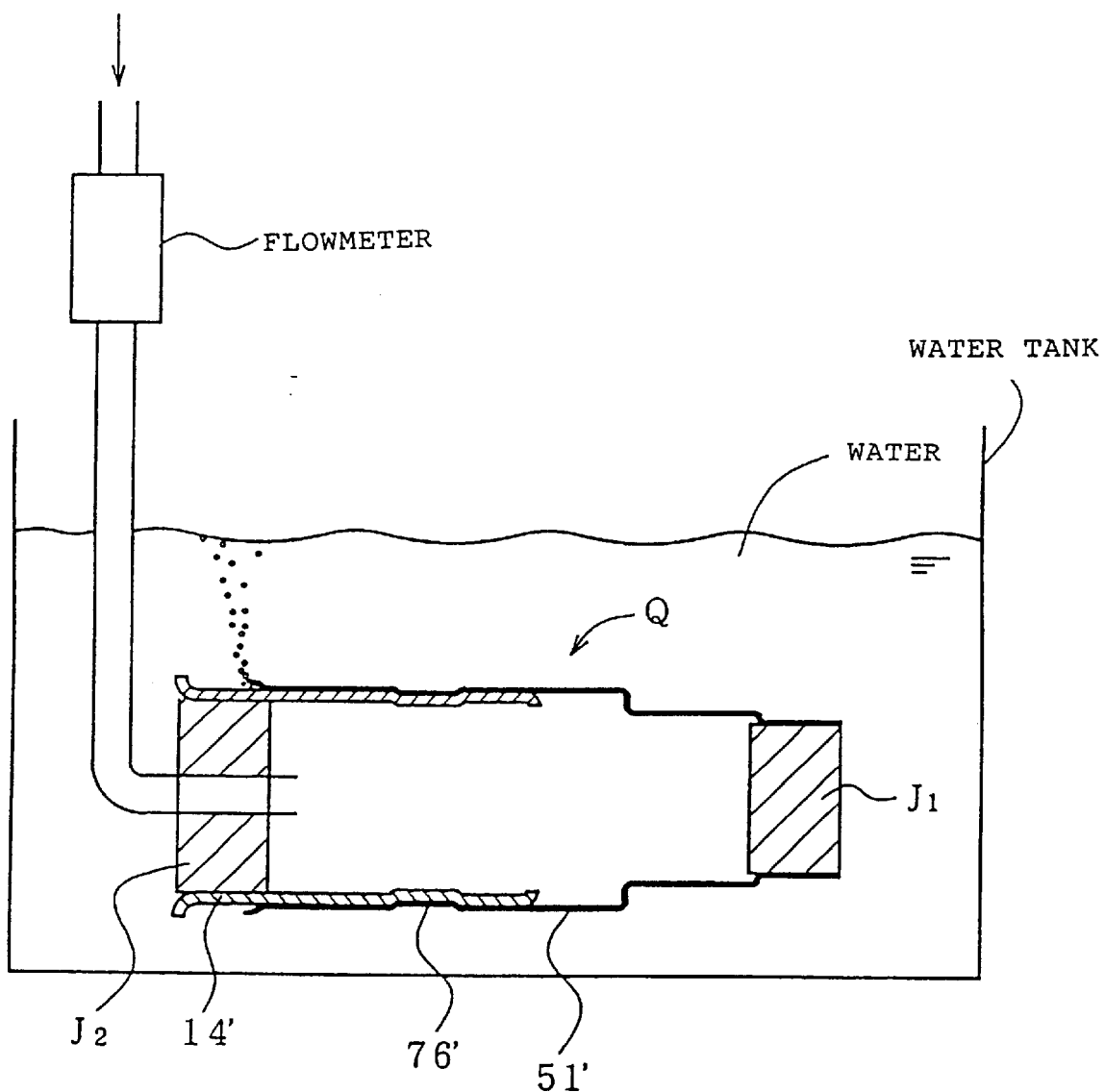
FIG. 17 shows an explanatory view depicting an airtightness test for the caulked portions.

As shown in FIG. 17, axially open end portions of the test assembly Q were plugged with rubber plugs J1 and J2; an air feed pipe was inserted through the plug J2 of the inner cylindrical member 14'; and the entire test assembly Q was submerged in water contained in a water tank. Subsequently, compressed air of 1.0 kgf/cm$^2$ in gauge pressure was fed into the interior of the test assembly Q through the air feed pipe. The gap between the inner cylindrical member 14' and the outer cylindrical member 51' was visually observed for any air leak, and a leak rate β (cc/minute) was measured by use of a volume flowmeter installed in the air feed pipe, thereby evaluating the airtightness of the caulked portion 76' and the auxiliary caulked portion 77'. The airtightness was evaluated and classified into the following 5 levels in terms of the leak rate β.

Figure 19:
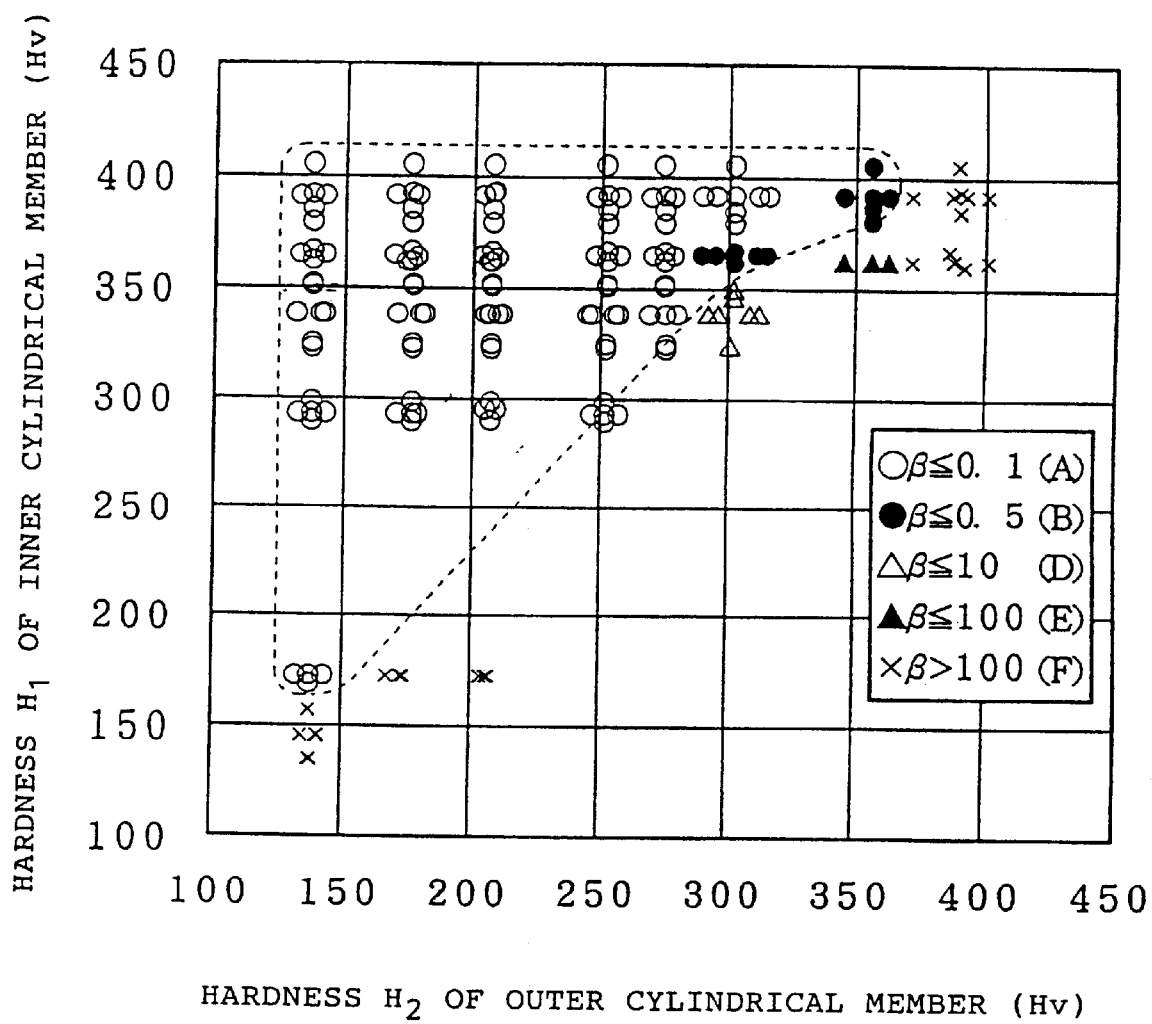
FIG. 19 is a graph showing the results of an airtightness test for combinations of hardness values of inner cylindrical members and outer cylindrical members (before exposure to heating-quenching cycles)

A: not greater than 6.1 cc/minute
B: not greater than 0.5 cc/minute
D: not greater than 10 cc/minute
E: not greater than 100 cc/minute
F: greater than 100 cc/minute Levels A and B were judged acceptable. In the graph of FIG. 19, the vertical axis represents the hardness H1 of the inner cylindrical member, and the horizontal axis represents the hardness H2 of the outer cylindrical member. The graph shows the results of evaluation of combinations of various values of H1 and H2. As seen from FIG. 19, acceptable airtightness is obtained in the following relatively wide range of H1 and H2. The hardness H1 of the inner cylindrical member is not less than Hv 170; the hardness H2 of the outer cylindrical member is not less than Hv 130; and the hardness difference "H1−H2" is not less than 50.

A thermal shock endurance test was conducted in the following manner. The test assemblies Q were subjected to 20 heat cycles, each cycle consisting of a step of heating the test assembly Q at a temperature of 500° C. for 60 minutes in the atmosphere and a step of immersing the heated assembly Q into water. Subsequently, the test assemblies Q were evaluated for airtightness according to the above method. The airtightness was evaluated and classified into the following 6 levels in terms of the leak rate β.

Figure 20:
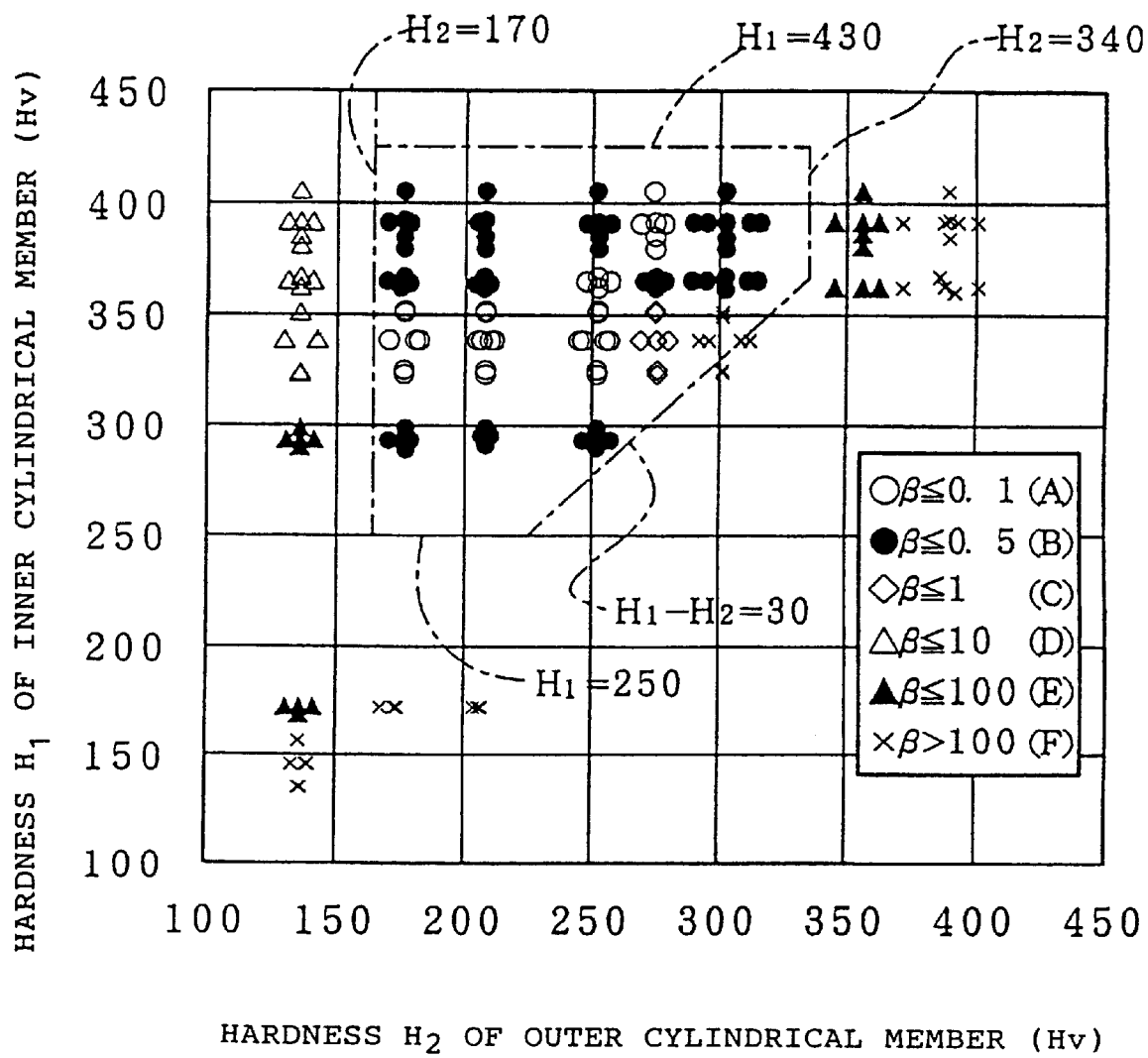
FIG. 20 is a graph showing the results of the airtightness test for combinations of hardness values of inner cylindrical members and outer cylindrical members (after exposure to heating quenching cycles).

A: not greater thin 0.1 cc/minute
B: not greater than 0.5 cc/minute
C: not greater than 1.0 cc/minute
D: not greater than 10 cc/minute
E: not greater than 100 cc/minute
F: greater than 100 cc/minute Levels A to B were judged acceptable. In the graph of FIG. 20, the vertical axis represents the hardness H1 of the inner cylindrical member, and the horizontal axis represents the hardness H2 of the outer cylindrical member. The graph shows the results of evaluation of combinations of various values of H1 and H2. As seen from FIG. 20, even after reception of thermal shocks, acceptable airtightness is maintained in the following range of H1 and H2 as described in the present invention. The hardness H1 of the inner cylindrical member is Hv 250 to 430; the hardness H2 of the outer cylindrical member is Hv 160 to 330; and the hardness difference "H1−H2" is not less than 30.

While preferred embodiments of the invention have been described, such description is for illustrative purposes only, and it should be understood that modifications and variations may be made without departing from the spirit and scope of the invention.

What is claimed is:

1. A gas sensor comprising:
   a sensing element having a sensing portion adapted to detect a component in a gas being measured;
   a ceramic separator having a flange-shaped support portion at an axially intermediate position; and
   a casing covering the sensing element while the gas being measured is permitted to flow through the casing to the sensing portion, the casing including at least two axially adjacent members, the at least two axially adjacent members having an inner member having a tip end portion and an outer member having an end portion, the tip end portion of the inner member disposed within the corresponding end portion of the outer member to thereby form an overlap zone, an inner surface of the tip end portion directly abutted to an outer surface of the flange-shaped support portion, wherein the inner member has a Vickers hardness H1 in the range of from Hv 250 to 430, the outer member has a Vickers hardness H2 in the range of from Hv 160 to 330, and the hardness difference "H1−H2" therebetween is not less than 30, and wherein in the overlap zone, the inner member and the outer member are circumferentially caulked in an airtight manner.

2. The gas sensor according to claim 1, wherein the Vickers hardness H1 of the inner member is not less than Hv 300, and the hardness difference "H1−H2" is not less than 50.

3. The gas sensor according to claim 1, wherein the thickness of the inner member is in the range of 0.6 mm to 1.0 mm, and the thickness of the outer member is in the range of 0.2 mm to 0.6 mm.

4. The gas sensor according to claim 1, wherein the Vickers hardness H2 of the outer member is in the range of Hv 175 to 275.

5. The gas sensor according to claim 1, wherein the inner member and the outer member are made of stainless steel.

6. The gas sensor according to claim 1, wherein the inner member and outer member are cylindrical.

7. The gas sensor according to claim 1, wherein the sensing element is bar-like and has an end portion, and wherein the sensing portion is formed at the end portion thereof.

8. The gas sensor according to claim 1, wherein the sensing element is cylindrical and has an end portion, and wherein the sensing portion is formed at the end portion thereof.

* * * * *